United States Patent
Haupt et al.

(10) Patent No.: US 8,710,059 B2
(45) Date of Patent: *Apr. 29, 2014

(54) N-PHENYL-(HOMO)PIPERAZINYL-BENZENESULFONYL OR BENZENESULFONAMIDE COMPOUNDS SUITABLE FOR TREATING DISORDERS THAT RESPOND TO THE MODULATION OF THE SEROTONIN 5-HT$_6$ RECEPTOR

(75) Inventors: Andreas Haupt, Ludwigshafen (DE); Frauke Pohlki, Ludwigshafen (DE); Liliane Unger, Ludwigshafen (DE); Ana Lucia Relo, Ludwigshafen (DE); Karsten Wicke, Ludwigshafen (DE); Min Zhang, Abbott Park, IL (US)

(73) Assignees: Abbott Laboratories, Abbott Park, IL (US); AbbVie Deutschland GmbH & Co. KG, Wiesbaden (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/286,446

(22) Filed: Nov. 1, 2011

(65) Prior Publication Data

US 2012/0142674 A1 Jun. 7, 2012

Related U.S. Application Data

(60) Provisional application No. 61/408,714, filed on Nov. 1, 2010.

(51) Int. Cl.
*A61K 31/495* (2006.01)
*C07D 241/04* (2006.01)

(52) U.S. Cl.
USPC ... 514/252.12; 544/358; 544/392; 514/252.1; 514/255.03

(58) Field of Classification Search
USPC .......... 544/336, 358, 392; 514/252.1, 252.12, 514/255.03
See application file for complete search history.

(56) References Cited

U.S. PATENT DOCUMENTS 6,281,214 B1 * 8/2001 Akasaka et al. ......... 514/253.01
6,316,450 B1 * 11/2001 Bromidge et al. ....... 514/253.05
8,076,326 B2 * 12/2011 Haupt et al. ............ 514/218
8,183,237 B2 * 5/2012 Haupt et al. ............ 514/218
8,343,959 B2 * 1/2013 Haupt et al. ............ 514/218
2003/0069254 A1 4/2003 Berger et al.

FOREIGN PATENT DOCUMENTS

| WO | 98/27081 | 6/1998 |
|---|---|---|
| WO | 99/02502 | 1/1999 |
| WO | 02/092585 | 11/2002 |
| WO | 2004/080986 | 9/2004 |
| WO | 2012/059432 | 5/2012 |

OTHER PUBLICATIONS

Bromidge et al (1999): STN International HCAPLUS database, Columbus (OH), accession No. 1999: 64780.*
International Search Report for Application No. PCT/EP2011/069009 dated Dec. 14, 2011 (5 pages).
International Preliminary Report on Patentability for Application No. PCT/EP2011/069009 dated May 16, 2013 (8 pages).

* cited by examiner

*Primary Examiner* — Golam M M Shameem
(74) *Attorney, Agent, or Firm* — Lisa V. Mueller; Michael Best & Friedrich LLP

(57) ABSTRACT

The present invention relates to N-Phenyl-(homo)piperazinyl-benzenesulfonyl or benzenesulfonamide compounds of formula I

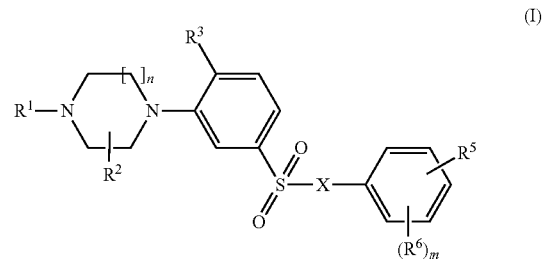

wherein the variables have the meanings given in the claims and the description, pharmaceutical compositions containing them, and their use in therapy. The compounds possess valuable therapeutic properties and are particularly suitable for treating diseases that respond to modulation of the serotonin 5-HT$_6$ receptor.

20 Claims, No Drawings

N-PHENYL-(HOMO)PIPERAZINYL-BENZENESULFONYL OR BENZENESULFONAMIDE COMPOUNDS SUITABLE FOR TREATING DISORDERS THAT RESPOND TO THE MODULATION OF THE SEROTONIN 5-HT$_6$ RECEPTOR

CROSS-REFERENCE TO RELATED APPLICATIONS

This claims priority to U.S. Provisional Patent Application No. 61/408,714, filed on Nov. 1, 2010, the contents of which are herein incorporated by reference.

BACKGROUND OF THE INVENTION

The present invention relates to N-Phenyl-(homo)piperazinyl-benzenesulfonyl or benzenesulfonamide compounds, pharmaceutical compositions containing them, and their use in therapy. The compounds possess valuable therapeutic properties and are particularly suitable for treating diseases that respond to modulation of the serotonin 5-HT$_6$ receptor.

Serotonin (5-hydroxytryptamine, 5-HT), a monoamine neurotransmitter and local hormone, is formed by the hydroxylation and decarboxylation of tryptophan. The greatest concentration is found in the enterochromaffin cells of the gastrointestinal tract, the remainder being predominantly present in platelets and in the Central Nervous System (CNS). 5-HT is implicated in a vast array of physiological and pathophysiological pathways. In the periphery, it contracts a number of smooth muscles and induces endothelium-dependent vasodilation. In the CNS, it is believed to be involved in a wide range of functions, including the control of appetite, mood, anxiety, hallucinations, sleep, vomiting and pain perception.

Neurons that secrete 5-HT are termed serotonergic. The function of 5-HT is exerted upon its interaction with specific (serotonergic) neurons. Until now, seven types of 5-HT receptors have been identified: 5-HT, (with subtypes 5-HT$_{1A}$, 5-HT$_{1B}$, 5-HT$_{1D}$, 5-HT$_{1E}$ and 5-HT$_{1F}$), 5-HT$_2$ (with subtypes 5-HT$_{2A}$, 5-HT$_{2B}$ and 5-HT$_{2C}$), 5-HT$_3$, 5-HT$_4$, 5-HT$_5$ (with subtypes 5-HT$_{5A}$ and 5-HT$_{5B}$), 5-HT$_6$ and 5-HT$_7$. Most of these receptors are coupled to G-proteins that affect the activities of either adenylate cyclase or phospholipase Cγ.

The human 5-HT$_6$ receptors are positively coupled to adenylyl cyclase. They are distributed throughout the limbic, striatal and cortical regions of the brain and show a high affinity to antipsychotics.

The modulation of the 5-HT$_6$ receptor by suitable substances is expected to improve certain disorders including cognitive dysfunctions, such as a deficit in memory, cognition and learning, in particular associated with Alzheimer's disease, age-related cognitive decline and mild cognitive impairment, attention deficit disorder/hyperactivity syndrome, personality disorders, such as schizophrenia, in particular cognitive deficits related with schizophrenia, affective disorders such as depression, anxiety and obsessive compulsive disorders, motion or motor disorders such as Parkinson's disease and epilepsy, migraine, sleep disorders (including disturbances of the Circadian rhythm), feeding disorders, such as anorexia and bulimia, certain gastrointestinal disorders such as Irritable Bowel Syndrome, diseases associated with neurodegeneration, such as stroke, spinal or head trauma and head injuries, such as hydrocephalus, addiction diseases and obesity (see e.g. A. Meneses, Drug News Perspect 14(7) (2001) pp. 396-400 and literature cited therein; J. Pharmacol. Sci. Vol. 101 (Suppl. 1), 2006, p. 124. Modulators of the 5HT$_6$-receptor such as PRX-07034 (Epix Pharmaceuticals) have been found in preclinical and clinical studies to be particular useful in the treatment of cognitive dysfunctions, in particular associated with Alzheimer's disease or schizophrenia or in the treatment of obesity (see e.g. http://www.epixpharma.com/products/prx-07034.asp).

WO 98/027081, WO 99/02502, WO 00/12623, WO 00/12073, US 2003/0069233, WO 02/08179, WO 02/92585, WO 2006/010629, WO 2007/118899 and WO 2007/118900 describe certain benzenesulfonanilide compounds having 5HT$_6$ receptor antagonist activity and suggest the use of these compounds for the treatment of medical disorders which are susceptible to the treatment with 5HT$_6$ receptor antagonists such as certain CNS disorders, drug abuse, ADHD, obesity and type II diabetes.

U.S. Pat. No. 6,825,202 and WO 03/014097 describe benzenesulfonyl compounds having 5HT$_6$ receptor activity.

However, there is still an ongoing need for providing compounds having high affinity for the 5-HT$_6$ receptor and which advantageously also show high selectivity to this receptor.

Besides the binding affinity for the 5-HT$_6$ receptor, further properties may be advantageous for the treatment and/or prophylaxis of 5-HT$_6$-dependent disorders, such as, for example:
1.) a selectivity for the 5-HT$_6$ receptor compared with the 5-HT$_{1A}$ receptor, i.e. the quotient of the binding affinity for the 5-HT$_{1A}$ receptor (Ki(5-HT$_{1A}$)) (determined in the unit "nanomolar (nM)") and the binding affinity for the 5-HT$_6$ receptor (Ki(5-HT$_6$)) (determined in the unit "nanomolar (nM)"). A larger quotient Ki(5-HT$_{1A}$)/Ki(5-HT$_6$) means a greater 5-HT$_6$ selectivity;
2.) a selectivity for the 5-HT$_6$ receptor compared with the 5-HT$_{2A}$ receptor, i.e. the quotient of the binding affinity for the 5-HT$_{2A}$ receptor (Ki(5-HT$_{2A}$)) (determined in the unit "nanomolar (nM)") and the binding affinity for the 5-HT$_6$ receptor (Ki(5-HT$_6$)) (determined in the unit "nanomolar (nM)"). A larger quotient Ki(5-HT$_{2A}$)/Ki(5-HT$_6$) means a greater 5-HT$_6$ selectivity.
3.) a selectivity for the 5-HT$_6$ receptor compared with the 5-HT$_{2B}$ receptor, i.e. the quotient of the binding affinity for the 5-HT$_{2B}$ receptor (Ki(5-HT$_{2B}$)) (determined in the unit "nanomolar (nM)") and the binding affinity for the 5-HT$_6$ receptor (Ki(5-HT$_6$)) (determined in the unit "nanomolar (nM)"). A larger quotient Ki(5-HT$_{2B}$)/Ki(5-HT$_6$) means a greater 5-HT$_6$ selectivity.
4.) a low affinity to adrenergic receptors, such as α$_1$-adrenergic receptor, histamine receptors, such as H$_1$-receptor, and dopaminergic receptors, such as D$_2$-receptor, in order to avoid or reduce considerable side effects associated with modulation of these receptors, such as postural hypotension, reflex tachycardia, potentiation of the anti-hypertensive effect of prazosin, terazosin, doxazosin and labetalol or dizziness associated to the blockade of the α$_1$-adrenergic receptor, weight gain, sedation, drowsiness or potentiation of central depressant drugs associated to the blockade of the H$_1$-receptor, or extrapyramidal movement disorder, such as dystonia, parkinsonism, akathisia, tardive dyskinesia or rabbit syndrome, or endocrine effects, such as prolactin elevation (galactorrhea, gynecomastia, menstruyl changes, sexual dysfunction in males), associated to the blockade of the D$_2$-receptor.
5.) the metabolic stability, for example determined from the half-lives, measured in vitro, in liver microsomes from various species (e.g. rat or human);
6.) no or only low inhibition of cytochrome P450 (CYP) enzymes: cytochrome P450 (CYP) is the name for a super-family of heme proteins having enzymatic activity (oxidase). They are also particularly important for the degradation (metabolism) of foreign substances such as drugs or xenobiotics in mammalian organisms. The principal representatives of the types and subtypes of CYP in the human body are: CYP 1A2, CYP 2C9, CYP 2D6 and CYP 3A4. If CYP 3A4 inhibitors (e.g. grapefruit juice, cimetidine, erythromycin) are used at the same time as medicinal substances which are degraded by this enzyme system and thus compete for the same binding site on the enzyme, the degradation thereof may be slowed down and thus effects and side effects of the administered medicinal substance may be undesirably enhanced;

7.) a suitable solubility in water (in mg/ml);

8.) suitable pharmacokinetics (time course of the concentration of the compound of the invention in plasma or in tissue, for example brain). The pharmacokinetics can be described by the following parameters: half-life (in h), volume of distribution (in l·kg$^{-1}$), plasma clearance (in l·h$^{-1}$·kg$^{-1}$), AUC (area under the curve, area under the concentration-time curve, in ng·h·l$^{-1}$), oral bioavailability (the dose-normalized ratio of AUC after oral administration and AUC after intravenous administration), the so-called brain-plasma ratio (the ratio of AUC in brain tissue and AUC in plasma);

9.) no or only low blockade of the hERG channel: compounds which block the hERG channel may cause a prolongation of the QT interval and thus lead to serious disturbances of cardiac rhythm (for example so-called "torsade de pointes"). The potential of compounds to block the hERG channel can be determined by means of the displacement assay with radio-labelled dofetilide which is described in the literature (G. J. Diaz et al., Journal of Pharmacological and Toxicological Methods, 50 (2004), 187-199). A smaller IC50 in this dofetilide assay means a greater probability of potent hERG blockade. In addition, the blockade of the hERG channel can be measured by electrophysiological experiments on cells which have been transfected with the hERG channel, by so-called whole-cell patch clamping (G. J. Diaz et al., Journal of Pharmacological and Toxicological Methods, 50 (2004), 187-199).

It is one object of the present invention to provide compounds which have a high affinity for the 5-HT$_6$ receptor. It is a further object of the present invention to provide compounds which selectively bind to the 5-HT$_6$ receptor. In addition, the substance of the invention should have one or more of the aforementioned advantages 1.) to 9.).

In particular, it is the object of the present invention to provide compounds which have a high affinity and selectivity for the 5-HT$_6$ receptor and which also show no or only low blockade of the hERG channel. The compounds should also have good pharmacological profile, e.g. a good bioavailability and/or a good metabolic stability.

SUMMARY OF THE INVENTION

The invention is based on the object of providing compounds which act as 5HT$_6$ receptor ligands. This object is achieved by compounds of formula I

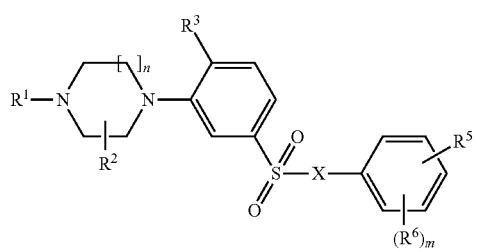

(I)

the stereoisomers, N-oxides, prodrugs, tautomers and/or physiologically tolerated acid addition salts thereof; and the compounds of the formula I, wherein at least one of the atoms has been replaced by its stable, non-radioactive isotope, wherein X is a bond or NR$^4$;

R$^1$ is selected from hydrogen, C$_1$-C$_4$-alkyl and fluorinated C$_1$-C$_4$-alkyl;

R$^2$ is selected from hydrogen and C$_1$-C$_4$-alkyl;

R$^3$ is selected from hydrogen, halogen, C$_1$-C$_4$-alkyl, fluorinated C$_1$-C$_4$-alkyl, C$_1$-C$_4$-alkoxy and fluorinated C$_1$-C$_4$-alkoxy;

R$^4$ is selected from hydrogen, C$_1$-C$_4$-alkyl and fluorinated C$_1$-C$_4$-alkyl;

R$^5$ is a group -A-[-O-B-]$_p$-O-R$^7$, wherein
A and B are independently of each other C$_1$-C$_4$-alkylene or fluorinated C$_1$-C$_4$-alkylene;
R$^7$ is C$_1$-C$_4$-alkyl or fluorinated C$_1$-C$_4$-alkyl; and
p is 0, 1, 2, 3, 4, 5 or 6;

R$^6$ is selected from halogen, C$_1$-C$_2$-alkyl, fluorinated C$_1$-C$_2$-alkyl, C$_1$-C$_2$-alkoxy and fluorinated C$_1$-C$_2$-alkoxy;

m is 0, 1 or 2; and n is 1 or 2.

The invention also relates to compounds of formula I or the stereoisomers, N-oxides, prodrugs, tautomers or physiologically tolerated acid addition salts thereof or to compounds of formula I, wherein at least one of the atoms has been replaced by its stable, non-radioactive isotope, for use as a medicament, and to compounds of formula I or the stereoisomers, N-oxides, prodrugs, tautomers or physiologically tolerated acid addition salts thereof for the treatment of a medical disorder susceptible to the treatment with a 5-HT$_6$ receptor ligand.

The invention furthermore relates to a pharmaceutical composition comprising at least one compound of formula I, a stereoisomer, N-oxide, prodrug, tautomer and/or physiologically tolerated acid addition salt thereof or at least one compound of formula I, wherein at least one of the atoms has been replaced by its stable, non-radioactive isotope, and at least one physiologically acceptable carrier and/or auxiliary substance.

The invention relates moreover to the use of compounds of formula I or of a stereoisomer, N-oxide, prodrug, tautomer or physiologically tolerated acid addition salt thereof or of a compound of formula I, wherein at least one of the atoms has been replaced by its stable, non-radioactive isotope, for the preparation of a medicament for the treatment of a medical disorder susceptible to the treatment with a 5-HT$_6$ receptor ligand, and to a method for treating a medical disorder susceptible to the treatment with a 5-HT$_6$ receptor ligand, said method comprising administering an effective amount of at least one compound of formula I or of a stereoisomer, N-oxide, prodrug, tautomer or physiologically tolerated acid addition salt thereof or of a compound of formula I, wherein at least one of the atoms has been replaced by its stable, non-radioactive isotope, or of a pharmaceutical composition as defined above to a subject in need thereof.

The present invention also relates to the compounds of formula I or a stereoisomer, N-oxide, prodrug, tautomer or physiologically tolerated acid addition salt thereof or a compound of formula I, wherein at least one of the atoms has been replaced by its stable, non-radioactive isotope, for use in modulating the 5-HT$_6$ receptor.

DETAILED DESCRIPTION OF THE INVENTION

The disorders and diseases which are susceptible to treatment with a compound of the formula I include, e.g., disorders and diseases of the central nervous system, in particular cognitive dysfunctions, such as a deficit in memory, cognition and learning, in particular associated with Alzheimer's disease, age-related cognitive decline and mild cognitive impairment, attention deficit disorder/hyperactivity syndrome (ADHD), personality disorders, such as schizophrenia, in particular cognitive deficits related with schizophrenia, affective disorders such as depression, anxiety and obsessive compulsive disorders, motion or motor disorders such as Parkinson's disease and epilepsy, migraine, sleep disorders (including disturbances of the Circadian rhythm), feeding disorders, such as anorexia and bulimia, certain gastrointestinal disorders such as Irritable Bowel Syndrome, diseases associated with neurodegeneration, such as stroke, spinal or head trauma and head injuries, including hydrocephalus, drug addiction and obesity.

Provided the compounds of the formula I of a given constitution may exist in different spatial arrangements, for example if they possess one or more centers of asymmetry, polysubstituted rings or double bonds, or as different tautomers, the invention also relates to enantiomeric mixtures, in particular racemates, diastereomeric mixtures and tautomeric mixtures, preferably, however, the respective essentially pure enantiomers (enantiomerically pure), diastereomers and tautomers of the compounds of formula I and/or of their salts and/or their N-oxides.

In the terms of the present invention, "prodrugs" are compounds which are metabolized in vivo to give the compounds of the invention of formula I. Typical examples for prodrugs are for example described in C. G. Wermeth (editor): The Practice of Medicinal Chemistry, Academic Press, San Diego, 1996, pages 671-715. Examples are phosphates, carbamates, aminoacids, esters, amides, peptides, urea and the like. In the present case, suitable prodrugs can be compounds of formula I wherein for example the nitrogen ring atom carrying the radical $R^1$ forms an amide/peptide bond in that this nitrogen atom is substituted by a $C_1$-$C_4$-alkylcarbonyl group, e.g. by acetyl, propionyl, n-propylcarbonyl, isopropylcarbonyl, n-butylcarbonyl or tert-butylcarbonyl (pivaloyl), by benzoyl, or by an aminoacid group bonded via CO, e.g. glycine, alanine, serine, phenylalanine and the like bonded via CO. Suitable prodrugs are furthermore alkylcarbonyloxy-alkylcarbamates, wherein said nitrogen atom carries a group —C(=O)—O—CHR$^x$—O—C(=O)—R$^y$, wherein R$^x$ and R$^y$ independently of each other are $C_1$-$C_4$-alkyl. These carbamate compounds are for example described in J. Alexander, R. Cargill, S. R. Michelson, H. Schwam, J. Medicinal Chem. 1988, 31(2), 318-322. These groups can be removed under metabolic conditions and result in compounds of formula I, wherein said nitrogen atom carries a hydrogen atom instead.

The invention also relates to physiologically tolerated salts of the compounds of the formula I, especially acid addition salts with physiologically tolerated acids. Examples of suitable physiologically tolerated organic and inorganic acids are hydrochloric acid, hydrobromic acid, phosphoric acid, sulfuric acid, $C_1$-$C_4$-alkylsulfonic acids, such as methanesulfonic acid, aromatic sulfonic acids, such as benzenesulfonic acid and toluenesulfonic acid, oxalic acid, maleic acid, fumaric acid, lactic acid, tartaric acid, adipic acid and benzoic acid. Other utilizable acids are described in Fortschritte der Arzneimittelforschung [Advances in drug research], Volume 10, pages 224 ff., Birkhäuser Verlag, Basel and Stuttgart, 1966.

The invention also relates to N-oxides of the compounds of the formula I, provided that those compounds contain a basic nitrogen atom, such as the nitrogen atom of the piperazine moiety.

The organic moieties mentioned in the above definitions of the variables are—like the term halogen—collective terms for individual listings of the individual group members. The prefix $C_n$-$C_m$ indicates in each case the possible number of carbon atoms in the group.

In the terms of the present invention, halogen is fluorine, chlorine, bromine or iodine, preferably fluorine or chlorine.

$C_1$-$C_2$-Alkyl is methyl or ethyl.

$C_1$-$C_3$-alkyl is methyl, ethyl, n-propyl or isopropyl.

$C_1$-$C_4$-Alkyl is a straight-chain or branched alkyl group having from 1 to 4 carbon atoms. Examples are methyl, ethyl, n-propyl, iso-propyl, n-butyl, 2-butyl, iso-butyl or tert-butyl.

Fluorinated $C_1$-$C_2$ alkyl is an alkyl group having 1 or 2 carbon atoms, wherein at least one, e.g. 1, 2, 3, 4 or all of the hydrogen atoms are replaced by a fluorine atom such as in fluoromethyl, difluoromethyl, trifluoromethyl, (R)-1-fluoroethyl, (S)-1-fluoroethyl, 2-fluoroethyl, 1,1-difluoroethyl, 2,2-difluoroethyl, 2,2,2-trifluoroethyl, 1,1,2,2-tetrafluoroethyl, or pentafluoroethyl.

Fluorinated $C_1$-$C_4$ alkyl is a straight-chain or branched alkyl group having from 1 to 4, in particular 1 to 3 carbon atoms (=fluorinated $C_1$-$C_3$ alkyl), wherein at least one, e.g. 1, 2, 3, 4 or all of the hydrogen atoms are replaced by a fluorine atom such as in fluoromethyl, difluoromethyl, trifluoromethyl, (R)-1-fluoroethyl, (S)-1-fluoroethyl, 2-fluoroethyl, 1,1-difluoroethyl, 2,2-difluoroethyl, 2,2,2-trifluoroethyl, 1,1,2,2-tetrafluoroethyl, (R)-1-fluoropropyl, (S)-1-fluoropropyl, 2-fluoropropyl, 3-fluoropropyl, 1,1-difluoropropyl, 2,2-difluoropropyl, 3,3-difluoropropyl, 3,3,3-trifluoropropyl, (R)-2-fluoro-1-methylethyl, (S)-2-fluoro-1-methylethyl, (R)-2,2-difluoro-1-methylethyl, (S)-2,2-difluoro-1-methylethyl, (R)-1,2-difluoro-1-methylethyl, (S)-1,2-difluoro-1-methylethyl, (R)-2,2,2-trifluoro-1-methylethyl, (S)-2,2,2-trifluoro-1-methylethyl, 2-fluoro-1-(fluoromethyl)ethyl, 1-(difluoromethyl)-2,2-difluoroethyl, 1-(trifluoromethyl)-2,2,2-trifluoroethyl, 1-(trifluoromethyl)-1,2,2,2-tetrafluoroethyl, (R)-1-fluorobutyl, (S)-1-fluorobutyl, 2-fluorobutyl, 3-fluorobutyl, 4-fluorobutyl, 1,1-difluorobutyl, 2,2-difluorobutyl, 3,3-difluorobutyl, 4,4-difluorobutyl, 4,4,4-trifluorobutyl, and the like.

$C_1$-$C_2$-Alkoxy is methoxy or ethoxy.

$C_1$-$C_3$-Alkoxy is methoxy, ethoxy, n-propoxy or isopropoxy.

$C_1$-$C_4$-Alkoxy is a straight-chain or branched alkyl group having from 1 to 4 carbon atoms, which is bound to the remainder of the molecule via an oxygen atom. Examples include methoxy, ethoxy, n-propoxy, isopropoxy, n-butoxy, 2-butoxy, iso-butoxy, and tert-butoxy.

Fluorinated $C_1$-$C_2$-alkoxy is an alkoxy group having from 1 or 2 carbon atoms, wherein at least one, e.g. 1, 2, 3, 4 or all of the hydrogen atoms are replaced by a fluorine atoms such as in fluoromethoxy, difluoromethoxy, trifluoromethoxy, (R)-1-fluoroethoxy, (S)-1-fluoroethoxy, 2-fluoroethoxy, 1,1-difluoroethoxy, 2,2-difluoroethoxy, 2,2,2-trifluoroethoxy, 1,1,2,2-tetrafluoroethoxy, or pentafluoroethoxy.

Fluorinated $C_1$-$C_4$-alkoxy is a straight-chain or branched alkoxy group having from 1 to 4 carbon atoms, wherein at least one, e.g. 1, 2, 3, 4 or all of the hydrogen atoms are replaced by a fluorine atoms such as in fluoromethoxy, difluoromethoxy, trifluoromethoxy, (R)-1-fluoroethoxy, (S)-1-fluoroethoxy, 2-fluoroethoxy, 1,1-difluoroethoxy, 2,2-difluoroethoxy, 2,2,2-trifluoroethoxy, 1,1,2,2-tetrafluoroethoxy, (R)-1-fluoropropoxy, (S)-1-fluoropropoxy, (R)-2-fluoropropoxy, (S)-2-fluoropropoxy, 3-fluoropropoxy, 1,1-difluoropropoxy, 2,2-difluoropropoxy, 3,3-difluoropropoxy, 3,3,3-trifluoropropoxy, (R)-2-fluoro-1-methylethoxy, (S)-2-fluoro-1-methylethoxy, (R)-2,2-difluoro-1-methylethoxy, (S)-2,2- difluoro-1-methylethoxy, (R)-1,2-difluoro-1-methylethoxy, (S)-1,2-difluoro-1-methylethoxy, (R)-2,2,2-trifluoro-1-methylethoxy, (S)-2,2,2-trifluoro-1-methylethoxy, 2-fluoro-1-(fluoromethyl)ethoxy, 1-(difluoromethyl)-2,2-difluoroethoxy, (R)-1-fluorobutoxy, (S)-1-fluorobutoxy, 2-fluorobutoxy, 3-fluorobutoxy, 4-fluorobutoxy, 1,1-difluorobutoxy, 2,2-difluorobutoxy, 3,3-difluorobutoxy, 4,4-difluorobutoxy, 4,4,4-trifluorobutoxy, and the like.

$C_1$-$C_6$-Alkoxy-$C_1$-$C_6$-alkyl is a straight-chain or branched alkyl group having from 1 to 6, especially 1 to 4 carbon atoms (=$C_1$-$C_6$-alkoxy-$C_1$-$C_4$-alkyl), in particular 1 to 3 carbon atoms (=$C_1$-$C_6$-alkoxy-$C_1$-$C_3$-alkyl), wherein one of the hydrogen atoms is replaced by a $C_1$-$C_6$-alkoxy group, such as in methoxymethyl, 1-methoxyethyl, 2-methoxyethyl, ethoxymethyl, 1-methoxypropyl, 2-methoxypropyl, 3-methoxypropyl, 1-ethoxypropyl, 2-ethoxypropyl, 3-ethoxypropyl and the like.

Fluorinated $C_1$-$C_6$-alkoxy-$C_1$-$C_6$-alkyl is a straight-chain or branched alkyl group having from 1 to 6, especially 1 to 4 carbon atoms (=fluorinated $C_1$-$C_6$-alkoxy-$C_1$-$C_4$-alkyl), in particular 1 to 3 carbon atoms (=fluorinated $C_1$-$C_6$-alkoxy-$C_1$-$C_3$-alkyl), wherein one of the hydrogen atoms is replaced by a $C_1$-$C_6$-alkoxy group and wherein at least one, e.g. 1, 2, 3, 4 or all of the hydrogen atoms (either in the alkoxy moiety or in the alkyl moiety or in both) are replaced by a fluorine atoms, such as in difluoromethoxymethyl ($CHF_2OCH_2$), trifluoromethoxymethyl, 1-difluoromethoxyethyl, 1-trifluoromethoxyethyl, 2-difluoromethoxyethyl, 2-trifluoromethoxyethyl, difluoro-methoxy-methyl ($CH_3OCF_2$), 1,1-difluoro-2-methoxyethyl, 2,2-difluoro-2-methoxyethyl and the like.

$C_1$-$C_2$-Alkylene is a hydrocarbon bridging group having 1 or 2 carbon atoms. Examples are methylene (—$CH_2$—), 1,1-ethylene (—$CH(CH_3)$—) and 1,2-ethylene (—$CH_2CH_2$—).

$C_2$-$C_3$-Alkylene is a hydrocarbon bridging group having 2 or 3 carbon atoms. Examples are 1,1-ethylene (—CH($CH_3$)—), 1,2-ethylene (—$CH_2CH_2$—), 1,1-propylene (—CH($CH_2CH_3$)—), 1,2-propylene (—$CH_2$—CH($CH_3$)— or —CH($CH_3$)—$CH_2$—) and 1,3-propylene (—$CH_2CH_2CH_2$—).

$C_1$-$C_4$-Alkylene is a hydrocarbon bridging group having 1, 2, 3 or 4 carbon atoms, like methylene, 1,1-ethylene, 1,2-ethylene, 1,1-propylene, 1,2-propylene, 1,3-propylene, 1,4-butylene (—$CH_2CH_2CH_2CH_2$—) and the like.

Fluorinated $C_1$-$C_4$-alkylene is a hydrocarbon bridging group having 1, 2, 3 or 4 carbon atoms, wherein at least one, e.g. 1, 2, 3, 4 or all of the hydrogen atoms are replaced by a fluorine atoms, like fluoromethylene, difluoromethylene 1-fluoro-1,1-ethylene, 2-fluoro-1,1-ethylene, 1,2-difluoro-1,1-ethylene, 2,2-difluoro-1,1-ethylene, 2,2,2-trifluoro-1,1-ethylene, 1-fluoro-1,2-ethylene, 2-fluoro-1,2-ethylene, 1,1-difluoro-1,2-ethylene, 1,2-difluoro-1,2-ethylene, and the like.

The remarks made above and in the following with respect to preferred aspects of the invention, e.g. to preferred meanings of the variables A, B, $R^1$, $R^2$, $R^3$, $R^4$, $R^5$, $R^6$, $R^7$, m and n of compounds I, to preferred compounds I and to preferred embodiments of the method or the use according to the invention, apply in each case on their own or in particular to combinations thereof.

In one preferred embodiment of the invention X is $NR^4$. In an alternatively preferred embodiment, X is a bond. More preferably, X is $NR^4$. In this case, $R^4$ has one of the above given general meanings or is preferably hydrogen or $C_1$-$C_4$-alkyl and more preferably hydrogen or methyl.

Preferably, $R^1$ is hydrogen, $C_1$-$C_4$-alkyl or fluorinated $C_1$-$C_3$-alkyl, e.g. hydrogen, methyl, ethyl or 2-fluoroethyl, more preferably hydrogen or $C_1$-$C_4$-alkyl, even more preferably hydrogen, methyl or ethyl and specifically hydrogen or methyl.

The radical $R^2$ replaces one hydrogen atom of the carbon ring atoms of the (homo)piperazine ring to which it is bound. $R^2$ is preferably hydrogen or methyl and more preferably hydrogen.

$R^3$ is preferably selected from hydrogen, $C_1$-$C_4$-alkyl, fluorinated $C_1$-$C_4$-alkyl, $C_1$-$C_4$-alkoxy and fluorinated $C_1$-$C_4$-alkoxy, more preferably from hydrogen, $C_1$-$C_4$-alkyl and $C_1$-$C_4$-alkoxy, even more preferably from methoxy, ethoxy, methyl and ethyl, in particular from methoxy, ethoxy and methyl, and is specifically methoxy or ethoxy.

Alternatively, $R^3$ is more preferably $C_1$-$C_4$-alkoxy and in particular methoxy or ethoxy.

$R^4$ is preferably hydrogen or $C_1$-$C_4$-alkyl, more preferably hydrogen or methyl and is specifically hydrogen.

In the radical $R^5$, A is preferably $C_1$-$C_2$-alkylene, more preferably methylene ($CH_2$) or 1,1-ethylene [CH($CH_3$)].

B is preferably $C_2$-$C_3$-alkylene, more preferably 1,2-ethylene or 1,2-propylene.

p is preferably 0.

$R^7$ is preferably $C_1$-$C_2$-alkyl or fluorinated $C_1$-$C_2$-alkyl.

Thus, the group A—[O—B—]$_p$—O—$R^7$ is preferably selected from $C_1$-$C_2$-alkoxy-$C_1$-$C_2$-alkyl and (fluorinated $C_1$-$C_2$-alkoxy)-$C_1$-$C_2$-alkyl.

$R^5$ is thus preferably selected from $C_1$-$C_2$-alkoxy-$C_1$-$C_2$-alkyl and (fluorinated $C_1$-$C_2$-alkoxy)-$C_1$-$C_2$-alkyl, even more preferably from $C_1$-$C_2$-alkoxy-methyl, 1-($C_1$-$C_2$-alkoxy)ethyl, (fluorinated $C_1$-$C_2$-alkoxy)-methyl and 1-(fluorinated $C_1$-$C_2$-alkoxy)-ethyl and particularly preferably from methoxymethyl, ethoxymethyl, 2,2,2-trifluoroethoxymethyl and 1-methoxyethyl. Specifically, $R^5$ is methoxymethyl.

In one preferred embodiment, $R^5$ is bound in the 2- or 3-position, more preferably in the 2-position, relative to the 1-position of the sulfonyl group $SO_2$—X.

In an alternatively preferred embodiment, $R^5$ is bound in the 4-position, relative to the 1-position of the sulfonyl group $SO_2$—X. The 2- or 3-position is however more preferred.

$R^6$ is preferably selected from F, Cl, methyl, difluoromethyl, trifluoromethyl, methoxy, difluoromethoxy and trifluoromethoxy and is more preferably methyl.

In case m is 1 and $R^5$ is bound in the 2- or 3-position, $R^6$ is preferably bound in the 5-position, relative to the 1-position of the sulfonyl group $SO_2$—X and to the 2- or 3-position of $R^5$. If m is 1 and $R^5$ is bound in the 2-position, $R^6$ may preferably also be bound in the 4-position, relative to the 1-position of the sulfonyl group $SO_2$—X and to the 2-position of $R^5$. But more preferably, if m is 1 and $R^5$ is bound in the 2-position, $R^6$ is preferably bound in the 5-position, relative to the 1-position of the sulfonyl group $SO_2$—X and to the 2-position of $R^5$.

m is preferably 0 or 1 and is specifically 0.

In one preferred embodiment, n is 1. In an alternatively preferred embodiment, n is 2. Specifically, n is 1.

The invention specifically relates to compounds of formula I.1,

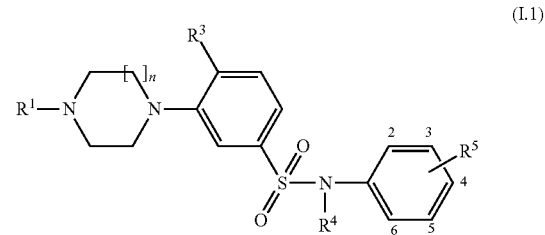

(I.1)

the stereoisomers, N-oxides, prodrugs, tautomers and/or physiologically tolerated acid addition salts thereof, wherein the combination of the variables is as defined in table 1 below:

TABLE 1

| No. | $R^1$ | $R^3$ | $R^4$ | $R^5$ | n |
|---|---|---|---|---|---|
| 1. | H | ethoxy | H | 3-methoxymethyl | 1 |
| 2. | $CH_3$ | ethoxy | H | 3-methoxymethyl | 1 |
| 3. | H | methoxy | H | 3-methoxymethyl | 1 |
| 4. | H | ethoxy | H | 2-methoxymethyl | 1 |
| 5. | H | methoxy | H | 2-methoxymethyl | 1 |
| 6. | $CH_3$ | methoxy | H | 3-methoxymethyl | 1 |
| 7. | $CH_3$ | ethoxy | H | 2-methoxymethyl | 1 |
| 8. | $CH_3$ | methoxy | H | 2-methoxymethyl | 1 |
| 9. | H | $CH_3$ | H | 3-methoxymethyl | 1 |
| 10. | $CH_3$ | $CH_3$ | H | 3-methoxymethyl | 1 |
| 11. | H | $CH_3$ | H | 2-methoxymethyl | 1 |
| 12. | $CH_3$ | $CH_3$ | H | 2-methoxymethyl | 1 |
| 13. | H | ethoxy | H | 4-methoxymethyl | 1 |
| 14. | $CH_3$ | ethoxy | H | 4-methoxymethyl | 1 |
| 15. | H | methoxy | H | 4-methoxymethyl | 1 |
| 16. | $CH_3$ | methoxy | H | 4-methoxymethyl | 1 |
| 17. | H | $CH_3$ | H | 4-methoxymethyl | 1 |
| 18. | $CH_3$ | $CH_3$ | H | 4-methoxymethyl | 1 |
| 19. | H | ethoxy | H | 3-ethoxymethyl | 1 |
| 20. | $CH_3$ | ethoxy | H | 3-ethoxymethyl | 1 |
| 21. | H | methoxy | H | 3-ethoxymethyl | 1 |
| 22. | H | ethoxy | H | 2-ethoxymethyl | 1 |
| 23. | H | methoxy | H | 2-ethoxymethyl | 1 |
| 24. | $CH_3$ | methoxy | H | 3-ethoxymethyl | 1 |
| 25. | $CH_3$ | ethoxy | H | 2-ethoxymethyl | 1 |
| 26. | $CH_3$ | methoxy | H | 2-ethoxymethyl | 1 |
| 27. | H | $CH_3$ | H | 3-ethoxymethyl | 1 |
| 28. | $CH_3$ | $CH_3$ | H | 3-ethoxymethyl | 1 |
| 29. | H | $CH_3$ | H | 2-ethoxymethyl | 1 |
| 30. | $CH_3$ | $CH_3$ | H | 2-ethoxymethyl | 1 |
| 31. | H | ethoxy | H | 4-ethoxymethyl | 1 |
| 32. | $CH_3$ | ethoxy | H | 4-ethoxymethyl | 1 |
| 33. | H | methoxy | H | 4-ethoxymethyl | 1 |
| 34. | $CH_3$ | methoxy | H | 4-ethoxymethyl | 1 |
| 35. | H | $CH_3$ | H | 4-ethoxymethyl | 1 |
| 36. | $CH_3$ | $CH_3$ | H | 4-ethoxymethyl | 1 |
| 37. | H | ethoxy | H | 3-(2,2,2-trifluoroethoxymethyl) | 1 |
| 38. | $CH_3$ | ethoxy | H | 3-(2,2,2-trifluoroethoxymethyl) | 1 |
| 39. | H | methoxy | H | 3-(2,2,2-trifluoroethoxymethyl) | 1 |
| 40. | H | ethoxy | H | 2-(2,2,2-trifluoroethoxymethyl) | 1 |
| 41. | H | methoxy | H | 2-(2,2,2-trifluoroethoxymethyl) | 1 |
| 42. | $CH_3$ | methoxy | H | 3-(2,2,2-trifluoroethoxymethyl) | 1 |
| 43. | $CH_3$ | ethoxy | H | 2-(2,2,2-trifluoroethoxymethyl) | 1 |
| 44. | $CH_3$ | methoxy | H | 2-(2,2,2-trifluoroethoxymethyl) | 1 |
| 45. | H | $CH_3$ | H | 3-(2,2,2-trifluoroethoxymethyl) | 1 |
| 46. | $CH_3$ | $CH_3$ | H | 3-(2,2,2-trifluoroethoxymethyl) | 1 |
| 47. | H | $CH_3$ | H | 2-(2,2,2-trifluoroethoxymethyl) | 1 |
| 48. | $CH_3$ | $CH_3$ | H | 2-(2,2,2-trifluoroethoxymethyl) | 1 |
| 49. | H | ethoxy | H | 4-(2,2,2-trifluoroethoxymethyl) | 1 |
| 50. | $CH_3$ | ethoxy | H | 4-(2,2,2-trifluoroethoxymethyl) | 1 |
| 51. | H | methoxy | H | 4-(2,2,2-trifluoroethoxymethyl) | 1 |
| 52. | $CH_3$ | methoxy | H | 4-(2,2,2-trifluoroethoxymethyl) | 1 |
| 53. | H | $CH_3$ | H | 4-(2,2,2-trifluoroethoxymethyl) | 1 |
| 54. | $CH_3$ | $CH_3$ | H | 4-(2,2,2-trifluoroethoxymethyl) | 1 |
| 55. | H | ethoxy | H | 3-(1-methoxyethyl) | 1 |
| 56. | $CH_3$ | ethoxy | H | 3-(1-methoxyethyl) | 1 |
| 57. | H | methoxy | H | 3-(1-methoxyethyl) | 1 |
| 58. | H | ethoxy | H | 2-(1-methoxyethyl) | 1 |
| 59. | H | methoxy | H | 2-(1-methoxyethyl) | 1 |
| 60. | $CH_3$ | methoxy | H | 3-(1-methoxyethyl) | 1 |
| 61. | $CH_3$ | ethoxy | H | 2-(1-methoxyethyl) | 1 |
| 62. | $CH_3$ | methoxy | H | 2-(1-methoxyethyl) | 1 |
| 63. | H | $CH_3$ | H | 3-(1-methoxyethyl) | 1 |
| 64. | $CH_3$ | $CH_3$ | H | 3-(1-methoxyethyl) | 1 |
| 65. | H | $CH_3$ | H | 2-(1-methoxyethyl) | 1 |
| 66. | $CH_3$ | $CH_3$ | H | 2-(1-methoxyethyl) | 1 |
| 67. | H | ethoxy | H | 4-(1-methoxyethyl) | 1 |
| 68. | $CH_3$ | ethoxy | H | 4-(1-methoxyethyl) | 1 |
| 69. | H | methoxy | H | 4-(1-methoxyethyl) | 1 |
| 70. | $CH_3$ | methoxy | H | 4-(1-methoxyethyl) | 1 |
| 71. | H | $CH_3$ | H | 4-(1-methoxyethyl) | 1 |
| 72. | $CH_3$ | $CH_3$ | H | 4-(1-methoxyethyl) | 1 |
| 73. | H | ethoxy | $CH_3$ | 3-methoxymethyl | 1 |
| 74. | $CH_3$ | ethoxy | $CH_3$ | 3-methoxymethyl | 1 |
| 75. | H | methoxy | $CH_3$ | 3-methoxymethyl | 1 |
| 76. | H | ethoxy | $CH_3$ | 2-methoxymethyl | 1 |
| 77. | H | methoxy | $CH_3$ | 2-methoxymethyl | 1 |
| 78. | $CH_3$ | methoxy | $CH_3$ | 3-methoxymethyl | 1 |
| 79. | $CH_3$ | ethoxy | $CH_3$ | 2-methoxymethyl | 1 |
| 80. | $CH_3$ | methoxy | $CH_3$ | 2-methoxymethyl | 1 |
| 81. | H | $CH_3$ | $CH_3$ | 3-methoxymethyl | 1 |
| 82. | $CH_3$ | $CH_3$ | $CH_3$ | 3-methoxymethyl | 1 |
| 83. | H | $CH_3$ | $CH_3$ | 2-methoxymethyl | 1 |
| 84. | $CH_3$ | $CH_3$ | $CH_3$ | 2-methoxymethyl | 1 |
| 85. | H | ethoxy | $CH_3$ | 4-methoxymethyl | 1 |
| 86. | $CH_3$ | ethoxy | $CH_3$ | 4-methoxymethyl | 1 |
| 87. | H | methoxy | $CH_3$ | 4-methoxymethyl | 1 |
| 88. | $CH_3$ | methoxy | $CH_3$ | 4-methoxymethyl | 1 |
| 89. | H | $CH_3$ | $CH_3$ | 4-methoxymethyl | 1 |
| 90. | $CH_3$ | $CH_3$ | $CH_3$ | 4-methoxymethyl | 1 |
| 91. | H | ethoxy | $CH_3$ | 3-ethoxymethyl | 1 |
| 92. | $CH_3$ | ethoxy | $CH_3$ | 3-ethoxymethyl | 1 |
| 93. | H | methoxy | $CH_3$ | 3-ethoxymethyl | 1 |
| 94. | H | ethoxy | $CH_3$ | 2-ethoxymethyl | 1 |
| 95. | H | methoxy | $CH_3$ | 2-ethoxymethyl | 1 |
| 96. | $CH_3$ | methoxy | $CH_3$ | 3-ethoxymethyl | 1 |
| 97. | $CH_3$ | ethoxy | $CH_3$ | 2-ethoxymethyl | 1 |
| 98. | $CH_3$ | methoxy | $CH_3$ | 2-ethoxymethyl | 1 |
| 99. | H | $CH_3$ | $CH_3$ | 3-ethoxymethyl | 1 |
| 100. | $CH_3$ | $CH_3$ | $CH_3$ | 3-ethoxymethyl | 1 |
| 101. | H | $CH_3$ | $CH_3$ | 2-ethoxymethyl | 1 |
| 102. | $CH_3$ | $CH_3$ | $CH_3$ | 2-ethoxymethyl | 1 |
| 103. | H | ethoxy | $CH_3$ | 4-ethoxymethyl | 1 |
| 104. | $CH_3$ | ethoxy | $CH_3$ | 4-ethoxymethyl | 1 |
| 105. | H | methoxy | $CH_3$ | 4-ethoxymethyl | 1 |
| 106. | $CH_3$ | methoxy | $CH_3$ | 4-ethoxymethyl | 1 |
| 107. | H | $CH_3$ | $CH_3$ | 4-ethoxymethyl | 1 |
| 108. | $CH_3$ | $CH_3$ | $CH_3$ | 4-ethoxymethyl | 1 |
| 109. | H | ethoxy | $CH_3$ | 3-(2,2,2-trifluoroethoxymethyl) | 1 |
| 110. | $CH_3$ | ethoxy | $CH_3$ | 3-(2,2,2-trifluoroethoxymethyl) | 1 |
| 111. | H | methoxy | $CH_3$ | 3-(2,2,2-trifluoroethoxymethyl) | 1 |
| 112. | H | ethoxy | $CH_3$ | 2-(2,2,2-trifluoroethoxymethyl) | 1 |
| 113. | H | methoxy | $CH_3$ | 2-(2,2,2-trifluoroethoxymethyl) | 1 |
| 114. | $CH_3$ | methoxy | $CH_3$ | 3-(2,2,2-trifluoroethoxymethyl) | 1 |
| 115. | $CH_3$ | ethoxy | $CH_3$ | 2-(2,2,2-trifluoroethoxymethyl) | 1 |
| 116. | $CH_3$ | methoxy | $CH_3$ | 2-(2,2,2-trifluoroethoxymethyl) | 1 |
| 117. | H | $CH_3$ | $CH_3$ | 3-(2,2,2-trifluoroethoxymethyl) | 1 |
| 118. | $CH_3$ | $CH_3$ | $CH_3$ | 3-(2,2,2-trifluoroethoxymethyl) | 1 |
| 119. | H | $CH_3$ | $CH_3$ | 2-(2,2,2-trifluoroethoxymethyl) | 1 |
| 120. | $CH_3$ | $CH_3$ | $CH_3$ | 2-(2,2,2-trifluoroethoxymethyl) | 1 |
| 121. | H | ethoxy | $CH_3$ | 4-(2,2,2-trifluoroethoxymethyl) | 1 |
| 122. | $CH_3$ | ethoxy | $CH_3$ | 4-(2,2,2-trifluoroethoxymethyl) | 1 |
| 123. | H | methoxy | $CH_3$ | 4-(2,2,2-trifluoroethoxymethyl) | 1 |
| 124. | $CH_3$ | methoxy | $CH_3$ | 4-(2,2,2-trifluoroethoxymethyl) | 1 |
| 125. | H | $CH_3$ | $CH_3$ | 4-(2,2,2-trifluoroethoxymethyl) | 1 |
| 126. | $CH_3$ | $CH_3$ | $CH_3$ | 4-(2,2,2-trifluoroethoxymethyl) | 1 |
| 127. | H | ethoxy | $CH_3$ | 3-(1-methoxyethyl) | 1 |
| 128. | $CH_3$ | ethoxy | $CH_3$ | 3-(1-methoxyethyl) | 1 |
| 129. | H | methoxy | $CH_3$ | 3-(1-methoxyethyl) | 1 |
| 130. | H | ethoxy | $CH_3$ | 2-(1-methoxyethyl) | 1 |
| 131. | H | methoxy | $CH_3$ | 2-(1-methoxyethyl) | 1 |
| 132. | $CH_3$ | methoxy | $CH_3$ | 3-(1-methoxyethyl) | 1 |
| 133. | $CH_3$ | ethoxy | $CH_3$ | 2-(1-methoxyethyl) | 1 |
| 134. | $CH_3$ | methoxy | $CH_3$ | 2-(1-methoxyethyl) | 1 |
| 135. | H | $CH_3$ | $CH_3$ | 3-(1-methoxyethyl) | 1 |
| 136. | $CH_3$ | $CH_3$ | $CH_3$ | 3-(1-methoxyethyl) | 1 |
| 137. | H | $CH_3$ | $CH_3$ | 2-(1-methoxyethyl) | 1 |
| 138. | $CH_3$ | $CH_3$ | $CH_3$ | 2-(1-methoxyethyl) | 1 |
| 139. | H | ethoxy | $CH_3$ | 4-(1-methoxyethyl) | 1 |
| 140. | $CH_3$ | ethoxy | $CH_3$ | 4-(1-methoxyethyl) | 1 |
| 141. | H | methoxy | $CH_3$ | 4-(1-methoxyethyl) | 1 |
| 142. | $CH_3$ | methoxy | $CH_3$ | 4-(1-methoxyethyl) | 1 |
| 143. | H | $CH_3$ | $CH_3$ | 4-(1-methoxyethyl) | 1 |
| 144. | $CH_3$ | $CH_3$ | $CH_3$ | 4-(1-methoxyethyl) | 1 |
| 145. | H | ethoxy | H | 3-methoxymethyl | 2 |
| 146. | $CH_3$ | ethoxy | H | 3-methoxymethyl | 2 |
| 147. | H | methoxy | H | 3-methoxymethyl | 2 |
| 148. | H | ethoxy | H | 2-methoxymethyl | 2 |
| 149. | H | methoxy | H | 2-methoxymethyl | 2 |
| 150. | $CH_3$ | methoxy | H | 3-methoxymethyl | 2 |
| 151. | $CH_3$ | ethoxy | H | 2-methoxymethyl | 2 |

TABLE 1-continued

| No. | R¹ | R³ | R⁴ | R⁵ | n |
|---|---|---|---|---|---|
| 152. | CH₃ | methoxy | H | 2-methoxymethyl | 2 |
| 153. | H | CH₃ | H | 3-methoxymethyl | 2 |
| 154. | CH₃ | CH₃ | H | 3-methoxymethyl | 2 |
| 155. | H | CH₃ | H | 2-methoxymethyl | 2 |
| 156. | CH₃ | CH₃ | H | 2-methoxymethyl | 2 |
| 157. | H | ethoxy | H | 4-methoxymethyl | 2 |
| 158. | CH₃ | ethoxy | H | 4-methoxymethyl | 2 |
| 159. | H | methoxy | H | 4-methoxymethyl | 2 |
| 160. | CH₃ | methoxy | H | 4-methoxymethyl | 2 |
| 161. | H | CH₃ | H | 4-methoxymethyl | 2 |
| 162. | CH₃ | CH₃ | H | 4-methoxymethyl | 2 |
| 163. | H | ethoxy | H | 3-ethoxymethyl | 2 |
| 164. | CH₃ | ethoxy | H | 3-ethoxymethyl | 2 |
| 165. | H | methoxy | H | 3-ethoxymethyl | 2 |
| 166. | H | ethoxy | H | 2-ethoxymethyl | 2 |
| 167. | H | methoxy | H | 2-ethoxymethyl | 2 |
| 168. | CH₃ | methoxy | H | 3-ethoxymethyl | 2 |
| 169. | CH₃ | ethoxy | H | 2-ethoxymethyl | 2 |
| 170. | CH₃ | methoxy | H | 2-ethoxymethyl | 2 |
| 171. | H | CH₃ | H | 3-ethoxymethyl | 2 |
| 172. | CH₃ | CH₃ | H | 3-ethoxymethyl | 2 |
| 173. | H | CH₃ | H | 2-ethoxymethyl | 2 |
| 174. | CH₃ | CH₃ | H | 2-ethoxymethyl | 2 |
| 175. | H | ethoxy | H | 4-ethoxymethyl | 2 |
| 176. | CH₃ | ethoxy | H | 4-ethoxymethyl | 2 |
| 177. | H | methoxy | H | 4-ethoxymethyl | 2 |
| 178. | CH₃ | methoxy | H | 4-ethoxymethyl | 2 |
| 179. | H | CH₃ | H | 4-ethoxymethyl | 2 |
| 180. | CH₃ | CH₃ | H | 4-ethoxymethyl | 2 |
| 181. | H | ethoxy | H | 3-(2,2,2-trifluoroethoxymethyl) | 2 |
| 182. | CH₃ | ethoxy | H | 3-(2,2,2-trifluoroethoxymethyl) | 2 |
| 183. | H | methoxy | H | 3-(2,2,2-trifluoroethoxymethyl) | 2 |
| 184. | H | ethoxy | H | 2-(2,2,2-trifluoroethoxymethyl) | 2 |
| 185. | H | methoxy | H | 2-(2,2,2-trifluoroethoxymethyl) | 2 |
| 186. | CH₃ | methoxy | H | 3-(2,2,2-trifluoroethoxymethyl) | 2 |
| 187. | CH₃ | ethoxy | H | 2-(2,2,2-trifluoroethoxymethyl) | 2 |
| 188. | CH₃ | methoxy | H | 2-(2,2,2-trifluoroethoxymethyl) | 2 |
| 189. | H | CH₃ | H | 3-(2,2,2-trifluoroethoxymethyl) | 2 |
| 190. | CH₃ | CH₃ | H | 3-(2,2,2-trifluoroethoxymethyl) | 2 |
| 191. | H | CH₃ | H | 2-(2,2,2-trifluoroethoxymethyl) | 2 |
| 192. | CH₃ | CH₃ | H | 2-(2,2,2-trifluoroethoxymethyl) | 2 |
| 193. | H | ethoxy | H | 4-(2,2,2-trifluoroethoxymethyl) | 2 |
| 194. | CH₃ | ethoxy | H | 4-(2,2,2-trifluoroethoxymethyl) | 2 |
| 195. | H | methoxy | H | 4-(2,2,2-trifluoroethoxymethyl) | 2 |
| 196. | CH₃ | methoxy | H | 4-(2,2,2-trifluoroethoxymethyl) | 2 |
| 197. | H | CH₃ | H | 4-(2,2,2-trifluoroethoxymethyl) | 2 |
| 198. | CH₃ | CH₃ | H | 4-(2,2,2-trifluoroethoxymethyl) | 2 |
| 199. | H | ethoxy | H | 3-(1-methoxyethyl) | 2 |
| 200. | CH₃ | ethoxy | H | 3-(1-methoxyethyl) | 2 |
| 201. | H | methoxy | H | 3-(1-methoxyethyl) | 2 |
| 202. | H | ethoxy | H | 2-(1-methoxyethyl) | 2 |
| 203. | H | methoxy | H | 2-(1-methoxyethyl) | 2 |
| 204. | CH₃ | methoxy | H | 3-(1-methoxyethyl) | 2 |
| 205. | CH₃ | ethoxy | H | 2-(1-methoxyethyl) | 2 |
| 206. | CH₃ | methoxy | H | 2-(1-methoxyethyl) | 2 |
| 207. | H | CH₃ | H | 3-(1-methoxyethyl) | 2 |
| 208. | CH₃ | CH₃ | H | 3-(1-methoxyethyl) | 2 |
| 209. | H | CH₃ | H | 2-(1-methoxyethyl) | 2 |
| 210. | CH₃ | CH₃ | H | 2-(1-methoxyethyl) | 2 |
| 211. | H | ethoxy | H | 4-(1-methoxyethyl) | 2 |
| 212. | CH₃ | ethoxy | H | 4-(1-methoxyethyl) | 2 |
| 213. | H | methoxy | H | 4-(1-methoxyethyl) | 2 |
| 214. | CH₃ | methoxy | H | 4-(1-methoxyethyl) | 2 |
| 215. | H | CH₃ | H | 4-(1-methoxyethyl) | 2 |
| 216. | CH₃ | CH₃ | H | 4-(1-methoxyethyl) | 2 |
| 217. | H | ethoxy | CH₃ | 3-methoxymethyl | 2 |
| 218. | CH₃ | ethoxy | CH₃ | 3-methoxymethyl | 2 |
| 219. | H | methoxy | CH₃ | 3-methoxymethyl | 2 |
| 220. | H | ethoxy | CH₃ | 2-methoxymethyl | 2 |
| 221. | H | methoxy | CH₃ | 2-methoxymethyl | 2 |
| 222. | CH₃ | methoxy | CH₃ | 3-methoxymethyl | 2 |
| 223. | CH₃ | ethoxy | CH₃ | 2-methoxymethyl | 2 |
| 224. | CH₃ | methoxy | CH₃ | 2-methoxymethyl | 2 |
| 225. | H | CH₃ | CH₃ | 3-methoxymethyl | 2 |
| 226. | CH₃ | CH₃ | CH₃ | 3-methoxymethyl | 2 |
| 227. | H | CH₃ | CH₃ | 2-methoxymethyl | 2 |
| 228. | CH₃ | CH₃ | CH₃ | 2-methoxymethyl | 2 |
| 229. | H | ethoxy | CH₃ | 4-methoxymethyl | 2 |
| 230. | CH₃ | ethoxy | CH₃ | 4-methoxymethyl | 2 |
| 231. | H | methoxy | CH₃ | 4-methoxymethyl | 2 |
| 232. | CH₃ | methoxy | CH₃ | 4-methoxymethyl | 2 |
| 233. | H | CH₃ | CH₃ | 4-methoxymethyl | 2 |
| 234. | CH₃ | CH₃ | CH₃ | 4-methoxymethyl | 2 |
| 235. | H | ethoxy | CH₃ | 3-ethoxymethyl | 2 |
| 236. | CH₃ | ethoxy | CH₃ | 3-ethoxymethyl | 2 |
| 237. | H | methoxy | CH₃ | 3-ethoxymethyl | 2 |
| 238. | H | ethoxy | CH₃ | 2-ethoxymethyl | 2 |
| 239. | H | methoxy | CH₃ | 2-ethoxymethyl | 2 |
| 240. | CH₃ | methoxy | CH₃ | 3-ethoxymethyl | 2 |
| 241. | CH₃ | ethoxy | CH₃ | 2-ethoxymethyl | 2 |
| 242. | CH₃ | methoxy | CH₃ | 2-ethoxymethyl | 2 |
| 243. | H | CH₃ | CH₃ | 3-ethoxymethyl | 2 |
| 244. | CH₃ | CH₃ | CH₃ | 3-ethoxymethyl | 2 |
| 245. | H | CH₃ | CH₃ | 2-ethoxymethyl | 2 |
| 246. | CH₃ | CH₃ | CH₃ | 2-ethoxymethyl | 2 |
| 247. | H | ethoxy | CH₃ | 4-ethoxymethyl | 2 |
| 248. | CH₃ | ethoxy | CH₃ | 4-ethoxymethyl | 2 |
| 249. | H | methoxy | CH₃ | 4-ethoxymethyl | 2 |
| 250. | CH₃ | methoxy | CH₃ | 4-ethoxymethyl | 2 |
| 251. | H | CH₃ | CH₃ | 4-ethoxymethyl | 2 |
| 252. | CH₃ | CH₃ | CH₃ | 4-ethoxymethyl | 2 |
| 253. | H | ethoxy | CH₃ | 3-(2,2,2-trifluoroethoxymethyl) | 2 |
| 254. | CH₃ | ethoxy | CH₃ | 3-(2,2,2-trifluoroethoxymethyl) | 2 |
| 255. | H | methoxy | CH₃ | 3-(2,2,2-trifluoroethoxymethyl) | 2 |
| 256. | H | ethoxy | CH₃ | 2-(2,2,2-trifluoroethoxymethyl) | 2 |
| 257. | H | methoxy | CH₃ | 2-(2,2,2-trifluoroethoxymethyl) | 2 |
| 258. | CH₃ | methoxy | CH₃ | 3-(2,2,2-trifluoroethoxymethyl) | 2 |
| 259. | CH₃ | ethoxy | CH₃ | 2-(2,2,2-trifluoroethoxymethyl) | 2 |
| 260. | CH₃ | methoxy | CH₃ | 2-(2,2,2-trifluoroethoxymethyl) | 2 |
| 261. | H | CH₃ | CH₃ | 3-(2,2,2-trifluoroethoxymethyl) | 2 |
| 262. | CH₃ | CH₃ | CH₃ | 3-(2,2,2-trifluoroethoxymethyl) | 2 |
| 263. | H | CH₃ | CH₃ | 2-(2,2,2-trifluoroethoxymethyl) | 2 |
| 264. | CH₃ | CH₃ | CH₃ | 2-(2,2,2-trifluoroethoxymethyl) | 2 |
| 265. | H | ethoxy | CH₃ | 4-(2,2,2-trifluoroethoxymethyl) | 2 |
| 266. | CH₃ | ethoxy | CH₃ | 4-(2,2,2-trifluoroethoxymethyl) | 2 |
| 267. | H | methoxy | CH₃ | 4-(2,2,2-trifluoroethoxymethyl) | 2 |
| 268. | CH₃ | methoxy | CH₃ | 4-(2,2,2-trifluoroethoxymethyl) | 2 |
| 269. | H | CH₃ | CH₃ | 4-(2,2,2-trifluoroethoxymethyl) | 2 |
| 270. | CH₃ | CH₃ | CH₃ | 4-(2,2,2-trifluoroethoxymethyl) | 2 |
| 271. | H | ethoxy | CH₃ | 3-(1-methoxyethyl) | 2 |
| 272. | CH₃ | ethoxy | CH₃ | 3-(1-methoxyethyl) | 2 |
| 273. | H | methoxy | CH₃ | 3-(1-methoxyethyl) | 2 |
| 274. | H | ethoxy | CH₃ | 2-(1-methoxyethyl) | 2 |
| 275. | H | methoxy | CH₃ | 2-(1-methoxyethyl) | 2 |
| 276. | CH₃ | methoxy | CH₃ | 3-(1-methoxyethyl) | 2 |
| 277. | CH₃ | ethoxy | CH₃ | 2-(1-methoxyethyl) | 2 |
| 278. | CH₃ | methoxy | CH₃ | 2-(1-methoxyethyl) | 2 |
| 279. | H | CH₃ | CH₃ | 3-(1-methoxyethyl) | 2 |
| 280. | CH₃ | CH₃ | CH₃ | 3-(1-methoxyethyl) | 2 |
| 281. | H | CH₃ | CH₃ | 2-(1-methoxyethyl) | 2 |
| 282. | CH₃ | CH₃ | CH₃ | 2-(1-methoxyethyl) | 2 |
| 283. | H | ethoxy | CH₃ | 4-(1-methoxyethyl) | 2 |
| 284. | CH₃ | ethoxy | CH₃ | 4-(1-methoxyethyl) | 2 |
| 285. | H | methoxy | CH₃ | 4-(1-methoxyethyl) | 2 |
| 286. | CH₃ | methoxy | CH₃ | 4-(1-methoxyethyl) | 2 |
| 287. | H | CH₃ | CH₃ | 4-(1-methoxyethyl) | 2 |
| 288. | CH₃ | CH₃ | CH₃ | 4-(1-methoxyethyl) | 2 |

Among these, preference is given to compounds no. 1, 2, 3, 4, 5, 6, 7, 8, 9, 10, 11, 12, 15, 21, 39, 57, 75, 147, 149, 150 and 152. More preference is given to compounds no. 1, 2, 3, 4, 5, 6, 7, 8, 9, 10, 11, 12, 15, 21, 39, 57 and 75.

The compounds I according to the invention can be prepared in analogy with methods known from in the art. An important approach to the compounds according to the invention wherein X is NR⁴ is the reaction of a 1-(piperazin-1-yl) or 1-(homopiperazin-1-yl) compound 1 where R³ is e.g. methyl, methoxy or ethoxy with chlorosulfonic acid and subsequent reaction of the intermediate sulfonyl chloride with an aniline derivative 4 as depicted in scheme 1.

Scheme 1:

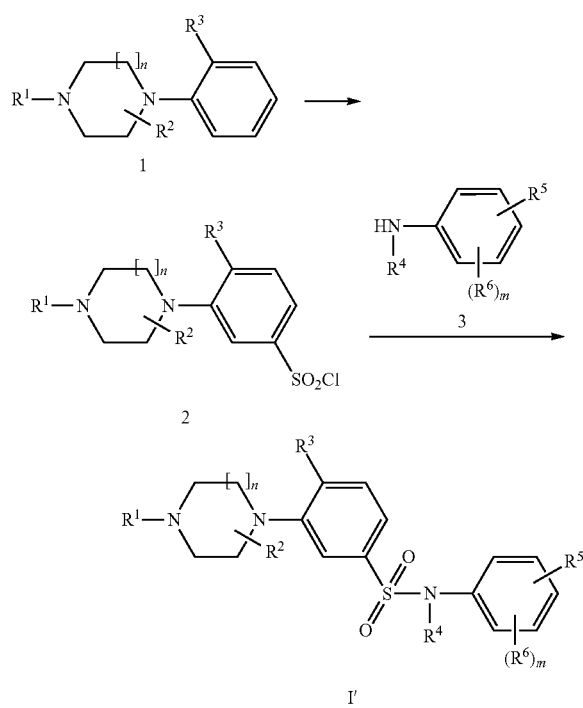

In scheme 1, $R^a$ is a nitrogen protecting group or methyl. Suitable N-protecting groups are described, for example, in P. J. Kocienski "Protecting Groups", $2^{nd}$ ed., Georg Thieme Verlag, Stuttgart 2000, pp 186-237 and in the literature cited therein. Preferred examples of N-protecting groups are e.g. oxycarbonyl groups such as $C_1$-$C_6$-alkoxycarbonyl, e.g. methoxycarbonyl, ethoxycarbonyl and Boc (tert-butoxycarbonyl) and other oxycarbonyl groups such as benzyloxycarbonyl (Cbz), allyloxycarbonyl, 9-fluorenylmethoxycarbonyl (Fmoc) and 2-trimethylsilylethoxycarbonyl (Teoc), or 2-propenyl (allyl). Especially preferred for introduction of a sulfonylchloride group is the trifluoroacetyl group as a protecting group for the piperazine or homopiperazine nitrogen.

The reaction depicted in scheme 1 takes place under the reaction conditions which are customary for preparing arylsulfonamide compounds or arylsulfonic esters, respectively, and which are described, for example, in J. March, Advanced Organic Chemistry, $3^{rd}$ edition, John Wiley & Sons, New York, 1985 p 444 and the literature cited therein, European J. Org. Chem. 2002 (13), pp. 2094-2108, Tetrahedron 2001, 57 (27) pp. 5885-5895, Bioorganic and Medicinal Chemistry Letters, 2000, 10(8), pp. 835-838 and Synthesis 2000 (1), pp. 103-108.

The reaction customarily takes place in an inert solvent, for example in an ether, such as diethyl ether, diisopropyl ether, methyl tert-butyl ether or tetrahydrofuran, a halohydrocarbon, such as dichloromethane, an aliphatic or cycloaliphatic hydrocarbon, such as pentane, hexane or cyclohexane, or an aromatic hydrocarbon, such as toluene, xylene, cumene and the like, or in a mixture of the abovementioned solvents. The reaction of compound 2 with compound 3 is customarily carried out in the presence of an auxiliary base. Suitable bases are inorganic bases, such as sodium carbonate or potassium carbonate, or sodium hydrogen carbonate or potassium hydrogen carbonate, and organic bases, for example trialkylamines, such as triethylamine, or pyridine compounds, such as pyridine, lutidine, 4-dimethylamino-pyridine and the like. The latter compounds can at the same time serve as solvents. The auxiliary base is customarily employed in at least equimolar quantities, based on the amine compound II.

The reaction of compound 2 with compound 3 yields compound I', which, in case $R^a$ is an N-protecting group, is deprotected to yield the compound of the general formula I, wherein $R^1$ is hydrogen. Deprotection of the compound I' can be achieved by standard methods, e.g. by the methods as described in P. J. Kocienski "Protecting Groups", $2^{nd}$ ed., Georg Thieme Verlag, Stuttgart 2000, pp 186-237 and in the literature cited therein.

Customary methods can then be used to react these compounds with a methylating agent such as methyl iodide or dimethyl sulfate resulting in a compound of the formula I in which $R^1$ is methyl. The reaction conditions which are required for this methylating reaction are disclosed, for example, in WO 02/083652, Tetrahedron 2000, 56(38) pp. 7553-7560 and Synlett. 2000 (4), pp. 475-480.

For preparing a compound of formula I in which $R^1$ is methyl, it is likewise possible to react a compound of formula I, in which $R^1$ is hydrogen, with formaldehyde in the presence of a reducing agent in a sense of a reductive amination. Suitable reducing agents are borohydrides such as sodium borohydride, sodium cyanoborohydride, sodium triacetoxyborohydride or borane-pyridine. The reductive amination is usually carried out in an organic solvent such as dichloromethane, 1,2-dichloroethane, tetrahydrofuran or acetonitrile.

Reaction of the compound I' with an alkylating agent yields a compound of the formula I' wherein $R^4$ is $C_1$-$C_4$-alkyl.

It is possible to react the compound I or I' with a methylating agent such as methyl iodide or dimethyl sulfate to yield a compound I or I' wherein $R^4$ is methyl.

If $R^a$ in such a compound is an N-protecting group, this is deprotected to yield the compound of the general formula I, wherein $R^1$ is hydrogen. Deprotection of the compound can be achieved by standard methods, e.g. by the methods as described in P. J. Kocienski "Protecting Groups", $2^{nd}$ ed., Georg Thieme Verlag, Stuttgart 2000, pp 186-237 and in the literature cited therein.

Sulfone compounds of the present invention where X is a bond can be prepared according to schemes 2 and 3, either from compounds 5 (which in itself can be prepared from aniline compounds 4 where the $NH_2$ group is transformed into a group $X^2$ which can either be e.g. iodine or bromine, via a Sandmeyer reaction) by reaction with a thiophenol compound 6 and subsequent oxidation of the sulfide (scheme 2) with suitable oxidizing agents such as oxone or peracids, or by reaction of a compound 5 with the salt of a sulfinic acid derivative 7 (usually the sodium salt) without the further need for an oxidative step (scheme 3; e.g. Synlett, 2003, 361 Cacchi et al.).

In schemes 2 and 3, $R^a$ is a nitrogen protecting group or methyl.

Scheme 2:

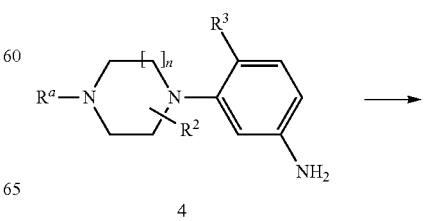

-continued

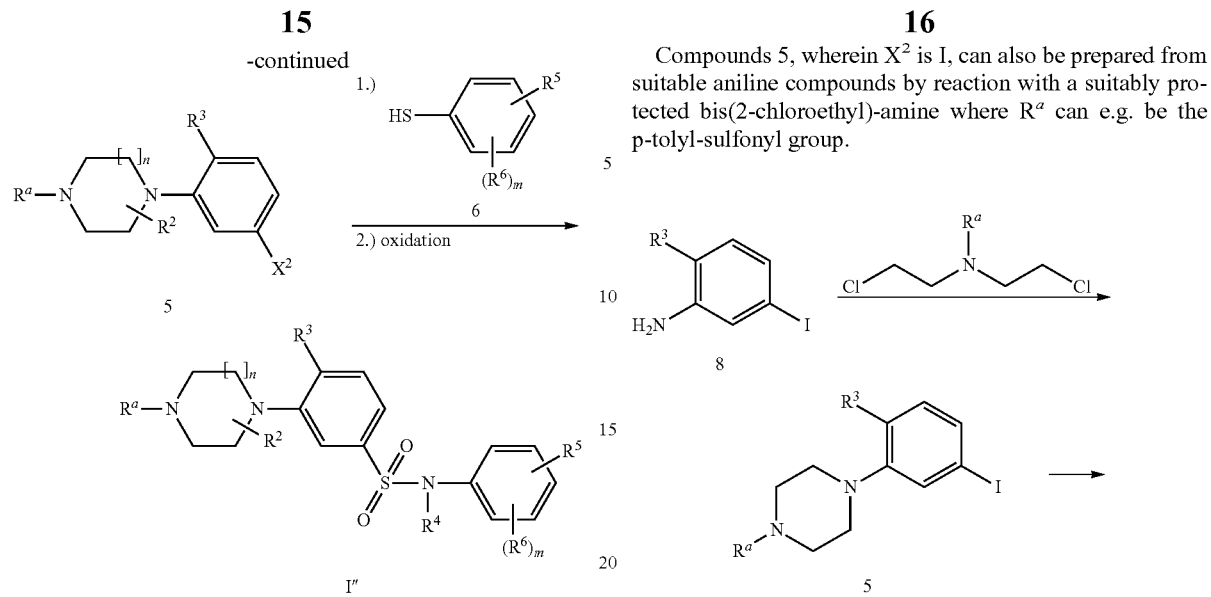

Scheme 3:

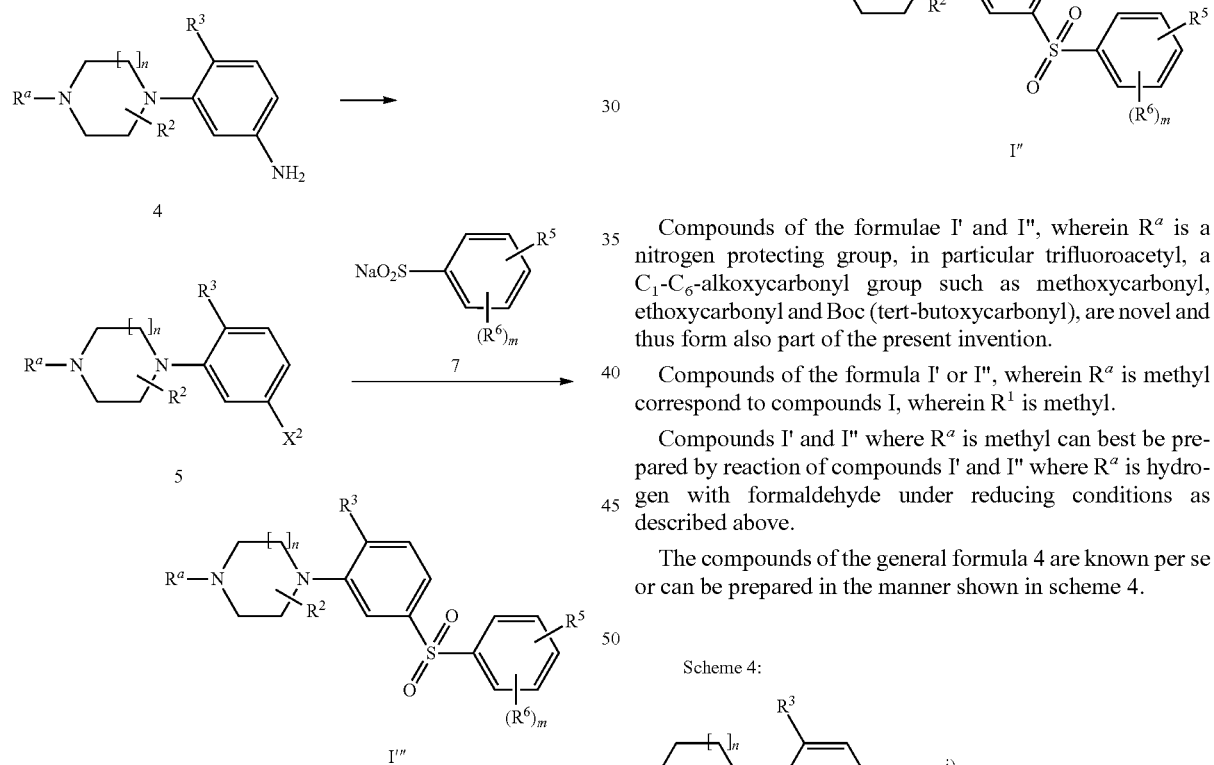

Compounds of formula I''' can be prepared by the palladium-catalyzed reaction of the sulfinic acid salt 7 with compounds 5, wherein $X^2$ is bromine or iodine. A suitable palladium catalyst is tris(dibenzylideneacetone)dipalladium(0) ($Pd_2(dba)_3$). The sulfone (IX) is usually prepared in the presence of Xantphos, a rigid bidendate ligand. The reaction is also usually carried out in the presence of n-tetrabutylammonium chloride. Sulfinate compounds 7 are either commercially available or can e.g. be prepared from the corresponding sulfonyl chlorides by reaction with sodium sulfite under basic conditions.

Compounds 5, wherein $X^2$ is I, can also be prepared from suitable aniline compounds by reaction with a suitably protected bis(2-chloroethyl)-amine where $R^a$ can e.g. be the p-tolyl-sulfonyl group.

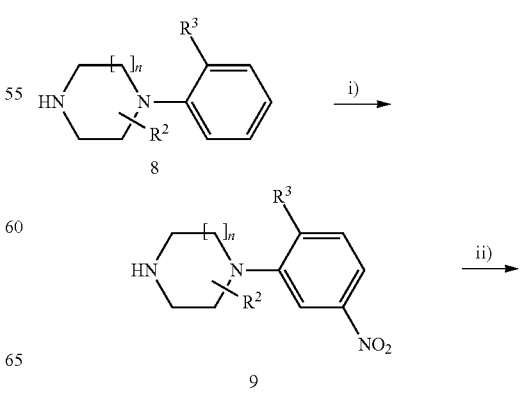

Compounds of the formulae I' and I'', wherein $R^a$ is a nitrogen protecting group, in particular trifluoroacetyl, a $C_1$-$C_6$-alkoxycarbonyl group such as methoxycarbonyl, ethoxycarbonyl and Boc (tert-butoxycarbonyl), are novel and thus form also part of the present invention.

Compounds of the formula I' or I'', wherein $R^a$ is methyl correspond to compounds I, wherein $R^1$ is methyl.

Compounds I' and I'' where $R^a$ is methyl can best be prepared by reaction of compounds I' and I'' where $R^a$ is hydrogen with formaldehyde under reducing conditions as described above.

The compounds of the general formula 4 are known per se or can be prepared in the manner shown in scheme 4.

Scheme 4:

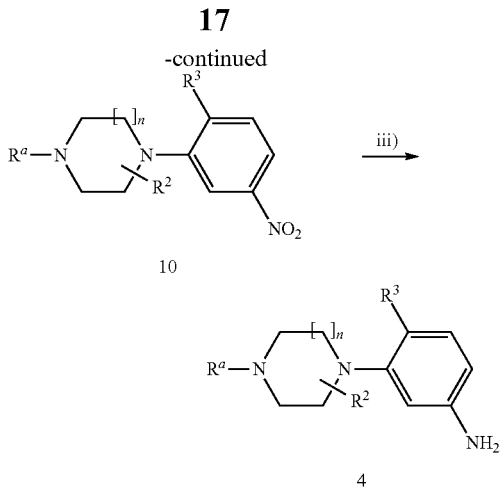

In step i) of scheme 4, the compound 8 is subjected to a nitration under standard conditions thereby yielding compound 9. Reaction conditions can be taken e.g. from U.S. Pat. No. 6,599,904 or from the working examples of the present application.

In step ii) of scheme 4, the NH-group of compound 9 is protected, either by a conventional N-protecting group as defined above or by introducing a methyl group via a methylating agent such as methyl bromide, methyl iodide or dimethyl sulfate. Introduction of an N-protecting group into compound 9 can be achieved by standard methods, e.g. by the methods as described in P. J. Kocienski "Protecting Groups", $2^{nd}$ ed., Georg Thieme Verlag, Stuttgart 2000, pp 186-237 and in the literature cited therein. Methylation of compound 9 is likewise achieved by standard methods of Organic chemistry.

In step iii), the nitro group in compound 10 is reduced to the $NH_2$ group to yield compound 4. The reaction conditions which are required for step iii) correspond to the customary conditions for reducing aromatic nitro groups which have been described extensively in the literature (see, for example, J. March, Advanced Organic Chemistry, 3rd ed., J. Wiley & Sons, New-York, 1985, p. 1183 and the literature cited in this reference). The reduction can be achieved, for example, by reacting the nitro compound 10 with a metal such as iron, zinc or tin under acidic reaction conditions, i.e. using nascent hydrogen, or using a complex hydride such as lithium aluminum hydride or sodium borohydride, preferably in the presence of transition metal compounds of nickel or cobalt such as $NiCl_2(P(phenyl)_3)_2$, or $CoCl_2$, (see Ono et al. Chem. Ind. (London), 1983 p. 480), or using $NaBH_2S_3$ (see Lalancette et al. Can. J. Chem. 49, 1971, p. 2990), with it being possible to carry out these reductions, depending on the given reagent, in substance or in a solvent or diluent. Alternatively, the reduction of 10 to 4 can be carried out with hydrogen in the presence of a transition metal catalyst, e.g. using hydrogen in the presence of catalysts based on platinum, palladium, nickel, ruthenium or rhodium. The catalysts can contain the transition metal in elemental form or in the form of a complex compound, of a salt or of an oxide of the transition metal, with it being possible, for the purpose of modifying the activity, to use customary coligands, e.g. organic phosphine compounds, such as triphenylphosphine, tricyclohexylphosphine or tri-n-butylphosphines or phosphites. The catalyst is customarily employed in quantities of from 0.001 to 1 mol per mol of compound 10, calculated as catalyst metal. In a preferred variant, the reduction is effected using tin(II) chloride in analogy with the methods described in Bioorganic and Medicinal Chemistry Letters, 2002, 12(15), pp. 1917-1919 and J. Med. Chem. 2002, 45(21), pp. 4679-4688. The reaction of 10 with tin(II) chloride is preferably carried out in an inert organic solvent, preferably an alcohol such as methanol, ethanol, isopropanol or butanol.

If not indicated otherwise, the above-described reactions are generally carried out in a solvent at temperatures between room temperature and the boiling temperature of the solvent employed. Alternatively, the activation energy which is required for the reaction can be introduced into the reaction mixture using microwaves, something which has proved to be of value, in particular, in the case of the reactions catalyzed by transition metals (with regard to reactions using microwaves, see Tetrahedron 2001, 57, p. 9199 ff. p. 9225 ff. and also, in a general manner, "Microwaves in Organic Synthesis", André Loupy (Ed.), Wiley-VCH 2002.

The acid addition salts of compounds I are prepared in a customary manner by mixing the free base with a corresponding acid, where appropriate in solution in an organic solvent, for example acetonitrile, a lower alcohol, such as methanol, ethanol or propanol, an ether, such as diethyl ether, methyl tert-butyl ether or diisopropyl ether, a ketone, such as acetone or methyl ethyl ketone, an ester, such as ethyl acetate, mixtures thereof as well as mixtures thereof with water.

The present invention moreover relates to compounds of formula I as defined above, wherein at least one of the atoms has been replaced by its stable, non-radioactive isotope (e.g., hydrogen by deuterium, $^{13}C$ by $^{13}C$, $^{14}N$ by $^{15}N$, $^{16}O$ by $^{18}O$) and preferably wherein at least one hydrogen atom has been replaced by a deuterium atom.

Of course, the compounds according to the invention contain more of the respective isotope than this naturally occurs and thus is anyway present in the compounds I.

Stable isotopes (e.g., deuterium, $^{13}C$, $^{15}N$, $^{18}O$) are nonradioactive isotopes which contain one additional neutron than the normally abundant isotope of the respective atom. Deuterated compounds have been used in pharmaceutical research to investigate the in vivo metabolic fate of the compounds by evaluation of the mechanism of action and metabolic pathway of the non-deuterated parent compound (Blake et al. J. Pharm. Sci. 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., J. Labelled Comp. Radiopharmaceut., 36(10):927-932 (1995); Kushner et al., Can. J. Physiol. Pharmacol., 77, 79-88 (1999).

Incorporation of a heavy atom particularly substitution of deuterium for hydrogen, can give rise to an isotope effect that could alter the pharmacokinetics of the drug. This effect is usually insignificant if the label is placed at a metabolically inert position of the molecule.

Stable isotope labeling of a drug can alter its physicochemical properties such as pKa and lipid solubility. These changes may influence the fate of the drug at different steps along its passage through the body. Absorption, distribution, metabolism or excretion can be changed. Absorption and distribution are processes that depend primarily on the molecular size and the lipophilicity of the substance. These effects and alterations can affect the pharmacodynamic response of the drug molecule if the isotopic substitution affects a region involved in a ligand-receptor interaction.

Drug metabolism can give rise to large isotopic effect if the breaking of a chemical bond to a deuterium atom is the rate limiting step in the process. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. In any reaction in which the breaking of this bond is the rate limiting step, the reaction will proceed slower for the molecule with the heavy isotope due to "kinetic isotope effect". A reaction involving breaking a C-D bond can be up to 700 percent slower than a similar reaction involving breaking a C—H bond. If the C-D bond is not involved in any of the steps leading to the metabolite, there may not be any effect to alter the behavior of the drug. If a deuterium is placed at a site involved in the metabolism of a drug, an isotope effect will be observed only if breaking of the C-D bond is the rate limiting step. There is evidence to suggest that whenever cleavage of an aliphatic C—H bond occurs, usually by oxidation catalyzed by a mixed-function oxidase, replacement of the hydrogen by deuterium will lead to observable isotope effect. It is also important to understand that the incorporation of deuterium at the site of metabolism slows its rate to the point where another metabolite produced by attack at a carbon atom not substituted by deuterium becomes the major pathway a process called "metabolic switching".

Deuterium tracers, such as deuterium-labeled drugs and doses, in some cases repeatedly, of thousands of milligrams of deuterated water, are also used in healthy humans of all ages, including neonates and pregnant women, without reported incident (e.g. Pons G and Rey E, Pediatrics 1999 104: 633; Coward W A et al., Lancet 1979 7: 13; Schwarcz H P, Control. Clin. Trials 1984 5(4 Suppl): 573; Rodewald L E et al., J. Pediatr. 1989 114: 885; Butte N F et al. Br. J. Nutr. 1991 65: 3; MacLennan A H et al. Am. J. Obstet Gynecol. 1981 139: 948). Thus, it is clear that any deuterium released, for instance, during the metabolism of compounds of this invention poses no health risk.

The weight percentage of hydrogen in a mammal (approximately 9%) and natural abundance of deuterium (approximately 0.015%) indicates that a 70 kg human normally contains nearly a gram of deuterium. Furthermore, replacement of up to about 15% of normal hydrogen with deuterium has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci. 1960 84: 736; Czakja D M et al., Am. J. Physiol. 1961 201: 357). Higher deuterium concentrations, usually in excess of 20%, can be toxic in animals. However, acute replacement of as high as 15%-23% of the hydrogen in humans' fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Increasing the amount of deuterium present in a compound above its natural abundance is called enrichment or deuterium-enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %.

The hydrogen atoms present on a particular organic compound have different capacities for exchange with deuterium. Certain hydrogen atoms are easily exchangeable under physiological conditions and, if replaced by deuterium atoms, it is expected that they will readily exchange for protons after administration to a patient. Certain hydrogen atoms may be exchanged for deuterium atoms by the action of a deuteric acid such as $D_2SO_4/D_2O$. Alternatively, deuterium atoms may be incorporated in various combinations during the synthesis of compounds of the invention. Certain hydrogen atoms are not easily exchangeable for deuterium atoms. However, deuterium atoms at the remaining positions may be incorporated by the use of deuterated starting materials or intermediates during the construction of compounds of the invention.

Deuterated and deuterium-enriched compounds of the invention can be prepared by using known methods described in the literature. Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure. Relevant procedures and intermediates are disclosed, for instance in Lizondo, J et al., *Drugs Fut,* 21(11), 1116 (1996); Brickner, S J et al., *J Med Chem,* 39(3), 673 (1996); Mallesham, B et al., *Org Lett,* 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; 20090082471, the methods are hereby incorporated by reference.

The present invention further relates to a pharmaceutical composition comprising at least one compound of formula I, a stereoisomer, prodrug, tautomer and/or physiologically tolerated acid addition salt thereof and optionally at least one physiologically acceptable carrier and/or auxiliary substance.

The invention relates moreover to the use of compounds of formula I or of a stereoisomer, N-oxide, prodrug, tautomer or physiologically tolerated acid addition salt thereof or of a compound of formula I, wherein at least one of the atoms has been replaced by its stable, non-radioactive isotope, for the preparation of a medicament for the treatment of a medical disorder susceptible to the treatment with a $5\text{-HT}_6$ receptor ligand, and to a method for treating a medical disorder susceptible to the treatment with a $5\text{-HT}_6$ receptor ligand, said method comprising administering an effective amount of at least one compound of formula I or of a stereoisomer, N-oxide, prodrug, tautomer or physiologically tolerated acid addition salt thereof or of a compound of formula I, wherein at least one of the atoms has been replaced by its stable, non-radioactive isotope, or of a pharmaceutical composition as defined above to a subject in need thereof.

The present invention also relates to the compounds of formula I or a stereoisomer, N-oxide, prodrug, tautomer or physiologically tolerated acid addition salt thereof or a compound of formula I, wherein at least one of the atoms has been replaced by its stable, non-radioactive isotope, for use in modulating the $5\text{-HT}_6$ receptor.

The compounds of the present invention can be a $5\text{-HT}_6$ receptor agonist, including partial agonistic activity, or a $5\text{-HT}_6$ receptor antagonist, including inverse agonist activity.

The compounds according to the present invention, as well as their salts and their N-oxides, have a surprisingly high affinity for $5\text{-HT}_6$ receptors. The high affinity of the compounds according to the invention for $5\text{-HT}_6$ receptors is reflected in very low in-vitro receptor binding constants ($K_i$ ($5\text{-HT}_6$) values) of as a rule less than 500, 100 or 50 nM (nmol/l), preferably of less than 10 nM and, in particular of less than 5 nM. The displacement of $^3$H-LSD can, for example, be used in receptor binding studies for determining binding affinities to $5\text{-HT}_6$ receptors.

Furthermore the compounds of the invention, as well as their salts and their N-oxides, are highly selective 5-HT$_6$ receptor ligands which, because of their low affinity for other receptors such as dopamine receptors, adrenergic receptors, muscarinic receptors, histamine receptors, opiate receptors, in particular dopamine D$_2$, α$_1$-adrenergic and histamine H$_1$ receptors, give rise to fewer side-effects than other, less selective 5-HT$_6$ ligands.

For instance the 5-HT$_6$/D$_2$, 5-HT$_6$/α$_1$-adrenergic or 5-HT$_6$/H$_1$ selectivities of the compounds according to the present invention, i.e. the ratios $K_i(D_2)/K_i$(5-HT$_6$), $K_i$(α$_1$-adrenergic)/$K_i$(5-HT$_6$) or $K_i(H_1)/K_i$(5-HT$_6$) of the receptor binding constants, is as a rule at least 25, preferably at least 50, even better at least 100.

The displacement of [$^3$H]SCH23390 or [$^{125}$I]spiperone can be used, for example, for carrying out receptor binding studies on D$_1$, D$_2$ and D$_4$ receptors.

Furthermore the compounds of the present invention because of their structural features are susceptible to display an enhanced brain penetration than other known 5-HT$_6$ receptor ligands.

Moreover, the compounds of the present invention because of their structural features show no or only low blockade of the hERG channel.

Because of their binding profile, the compounds of the present invention can be used for treating diseases which respond to 5-HT$_6$ receptor ligands (or which are susceptible to treatment with a 5-HT$_6$ receptor ligand), i.e. they are effective for treating those medical disorders or diseases in which exerting an influence on (modulating) the 5-HT$_6$ receptor leads to an improvement in the clinical picture or to the disease being cured. Examples of these diseases are disorders or diseases of the central nervous system.

Disorders or diseases of the central nervous system are understood as meaning disorders which affect the spinal cord and, in particular, the brain. Within the meaning of the invention, the term "disorder" denotes disturbances and/or anomalies which are as a rule regarded as being pathological conditions or functions and which can manifest themselves in the form of particular signs, symptoms and/or malfunctions. While the treatment according to the invention can be directed toward individual disorders, i.e. anomalies or pathological conditions, it is also possible for several anomalies, which may be causatively linked to each other, to be combined into patterns, i.e. syndromes, which can be treated in accordance with the invention.

The disorders which can be treated in accordance with the invention are in particular disorders which respond to a modulation of the 5-HT$_6$ receptor. They include cognitive dysfunctions, such as a deficit in memory, cognition and learning, in particular associated with Alzheimer's disease, age-related cognitive decline and mild cognitive impairment, attention deficit disorder/hyperactivity syndrome, personality disorders, such as schizophrenia, in particular cognitive deficits related with schizophrenia, affective disorders such as depression, anxiety and obsessive compulsive disorders, motion or motor disorders such as Parkinson's disease and epilepsy, migraine, sleep disorders (including disturbances of the Circadian rhythm), feeding disorders, such as anorexia and bulimia, certain gastrointestinal disorders such as Irritable Bowel Syndrome, diseases associated with neurodegeneration, such as stroke, spinal or head trauma and head injuries, such as hydrocephalus, addiction diseases including e.g. drug addiction and obesity.

The addiction diseases include psychic disorders and behavioral disturbances which are caused by the abuse of psychotropic substances, including certain pharmaceuticals, such as sedative, anxiolytica, hypnotics or narcotics (hereinafter also referred to as drug addiction), and also other addiction diseases, such as addiction to gaming (gambling; impulse control disorders not elsewhere classified). Examples of addictive substances are: opioids (e.g. morphine, heroin and codeine), cocaine; nicotine; alcohol; substances which interact with the GABA chloride channel complex, sedatives, hypnotics and tranquilizers, for example benzodiazepines; LSD; cannabinoids; psychomotor stimulants, such as 3,4-methylenedioxy-N-methylamphetamine (ecstasy); amphetamine and amphetamine-like substances such as methylphenidate and other stimulants including caffeine. Addictive substances which come particularly into consideration are opioids, cocaine, amphetamine or amphetamine-like substances, hallucinogens, NMDA-receptor antagonists such phencyclidine and related cyclidines, dextrometorphan, dextrorphan, ibogaine, ketimine and tiletamine, cannabis, nicotine and alcohol. Other addiction diseases include gaming (gambling), including problem gambling (compulsive gambling, ludomania), computer or video game addiction and internet addiction.

With regard to the treatment of addiction diseases, particular preference is given to those compounds according to the present invention which themselves do not possess any psychotropic effect. This can also be observed in a test using rats, which, after having been administered compounds which can be used in accordance with the invention, reduce their self administration of psychotropic substances, for example cocaine or alcohol.

According to another aspect of the present invention, the compounds according to the invention are suitable for treating disorders whose causes can at least partially be attributed to an anomalous activity of 5-HT$_6$ receptors.

According to another aspect of the present invention, the treatment is directed, in particular, toward those disorders which can be influenced, within the sense of an expedient medicinal treatment, by the binding of preferably exogeneously administered binding partners (ligands) to 5-HT$_6$ receptors.

The diseases which can be treated with the compounds according to the invention are frequently characterized by progressive development, i.e. the above-described conditions change over the course of time; as a rule, the severity increases and conditions may possibly merge into each other or other conditions may appear in addition to those which already exist.

The compounds of the present invention can be used to treat a large number of signs, symptoms and/or malfunctions which are connected with the disorders of the central nervous system and, in particular, the abovementioned conditions. These signs, symptoms and/or malfunctions include, for example, a disturbed relationship to reality, lack of insight and ability to meet customary social norms or the demands made by life, changes in temperament, changes in individual drives, such as hunger, sleep, thirst, etc., and in mood, disturbances in the ability to observe and combine, changes in personality, in particular emotional lability, hallucinations, ego-disturbances, distractedness, ambivalence, autism, depersonalization and false perceptions, delusional ideas, chanting speech, lack of synkinesia, short-step gait, flexed posture of trunk and limbs, tremor, poverty of facial expression, monotonous speech, depressions, apathy, impeded spontaneity and decisiveness, impoverished association ability, anxiety, nervous agitation, stammering, social phobia, panic disturbances, withdrawal symptoms in association with dependency, maniform syndromes, states of excitation and confusion, dysphoria, dyskinetic syndromes and tic disorders, e.g. Huntington's chorea and Gillesde-la-Tourette's syndrome, vertigo syndromes, e.g. peripheral positional, rotational and oscillatory vertigo, melancholia, hysteria, hypochondria and the like.

Within the meaning of the invention, a treatment also includes a preventive treatment (prophylaxis), in particular as relapse prophylaxis or phase prophylaxis, as well as the treatment of acute or chronic signs, symptoms and/or malfunctions. The treatment can be orientated symptomatically, for example as the suppression of symptoms. It can be effected over a short period, be orientated over the medium term or can be a long-term treatment, for example within the context of a maintenance therapy.

The compounds according to the invention are preferentially suitable for treating diseases of the central nervous system, more preferably for treating cognitive dysfunctions and in particular, for treating cognitive dysfunctions associated with schizophrenia or with Alzheimer's disease.

According to another aspect of the invention the compounds of the present invention are particularly suitable for treating addiction diseases caused for instance by the abuse of psychotropic substances, such as pharmaceuticals, narcotics, nicotine or alcohol, including psychic disorders and behavioral disturbances related thereto. The compounds of the present invention are likewise particularly suitable for treating addiction diseases which are not caused by the abuse of psychotropic substances, such as gaming (gambling), including problem gambling (compulsive gambling, ludomania), computer or video game addiction and internet addiction. With regard to addiction diseases, the compound of the present invention can be used for the therapy during addiction and also for preventing relapse into addiction.

According to another aspect of the invention the compounds of the invention, their salts and their N-oxides are particularly suitable for treating nutritional disorders, such as obesity, as well as diseases related thereto, such as cardiovascular diseases, digestive diseases, respiratory diseases, cancer or type 2 diabetes.

Within the context of the treatment, the use according to the invention of the described compounds involves a method. In this method, an effective quantity of one or more compounds, as a rule formulated in accordance with pharmaceutical and veterinary practice, is administered to the individual to be treated, preferably a mammal, in particular a human being, productive animal or domestic animal. Whether such a treatment is indicated, and in which form it is to take place, depends on the individual case and is subject to medical assessment (diagnosis) which takes into consideration signs, symptoms and/or malfunctions which are present, the risks of developing particular signs, symptoms and/or malfunctions, and other factors.

As a rule, the treatment is effected by means of single or repeated daily administration, where appropriate together, or alternating, with other active compounds or active compound-containing preparations such that a daily dose of preferably from about 0.1 to 1000 mg/kg of bodyweight, in the case of oral administration, or of from about 0.1 to 100 mg/kg of bodyweight, in the case of parenteral administration, is supplied to an individual to be treated.

The invention also relates to the production of pharmaceutical compositions for treating an individual, preferably a mammal, in particular a human being, productive animal or domestic animal. Thus, the compounds of the invention, their salts and/or their N-oxides are customarily administered in the form of pharmaceutical compositions which comprise a pharmaceutically acceptable excipient together with at least one compound according to the invention and, where appropriate, other active compounds. These compositions can, for example, be administered orally, rectally, transdermally, subcutaneously, intravenously, intramuscularly or intranasally.

Examples of suitable pharmaceutical formulations are solid medicinal forms, such as powders, granules, tablets, in particular film tablets, lozenges, sachets, cachets, sugar-coated tablets, capsules, such as hard gelatin capsules and soft gelatin capsules, suppositories or vaginal medicinal forms, semisolid medicinal forms, such as ointments, creams, hydrogels, pastes or plasters, and also liquid medicinal forms, such as solutions, emulsions, in particular oil-in-water emulsions, suspensions, for example lotions, injection preparations and infusion preparations, and eyedrops and eardrops. Implanted release devices can also be used for administering inhibitors according to the invention. In addition, it is also possible to use liposomes or microspheres.

When producing the compositions, the compounds according to the invention are optionally mixed or diluted with one or more excipients. Excipients can be solid, semisolid or liquid materials which serve as vehicles, carriers or medium for the active compound.

Suitable excipients are listed in the specialist medicinal monographs. In addition, the formulations can comprise pharmaceutically acceptable carriers or customary auxiliary substances, such as glidants; wetting agents; emulsifying and suspending agents; preservatives; antioxidants; antiirritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik and angrenzende Gebiete [Encyclopedia of auxiliary substances for pharmacy, cosmetics and related fields], $4^{th}$ edition, Aulendorf: ECV-Editio-Kantor-Verlag, 1996.

The following examples serve to explain the present invention without limiting its scope.

EXAMPLES

The compounds were either characterized via proton-NMR in $d_6$-dimethylsulfoxid or d-chloroform on a 400 MHz or 500 MHz NMR instrument (Bruker AVANCE), or by mass spectrometry, generally recorded via HPLC-MS in a fast gradient on C18-material (electrospray-ionisation (ESI) mode), or melting point.

The magnetic nuclear resonance spectral properties (NMR) refer to the chemical shifts ($\delta$) expressed in parts per million (ppm). The relative area of the shifts in the $^1$H NMR spectrum corresponds to the number of hydrogen atoms for a particular functional type in the molecule. The nature of the shift, as regards multiplicity, is indicated as singlet (s), broad

I. PREPARATION EXAMPLES

Example 1

N-(3-Methoxymethyl-phenyl)-4-methyl-3-piperazin-1-yl-benzenesulfonamide hydrochloride

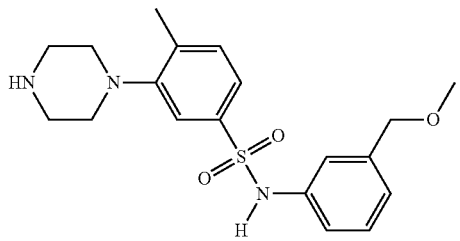 [SMILES: COCc1cccc(NS(=O)(=O)c2ccc(C)c(N3CCNCC3)c2)c1]

1.1 2,2,2-Trifluoro-1-(4-o-tolyl-piperazin-1-yl)-ethanone 29.9 g of 2,2,2-trifluoroacetic anhydride (104 mmol) were dissolved in 150 mL of dichloromethane, cooled to −20° C., and 20 g of 1-o-tolylpiperazine-1,4-diium chloride (80 mmol)—dissolved in 150 mL of dichloromethane—added dropwise. After stirring for 16 h at room temperature, 400 ml of ice water were added, the organic phase was separated, washed twice with water, and the pH adjusted to neutral with 1% aqueous sodium bicarbonate solution. The organic phase was washed with saturated aqueous sodium chloride, dried over sodium sulphate, filtered and the solvent evaporated to yield 21.5 g of product which crystallized upon cooling.

1.2 4-Methyl-3-[4-(2,2,2-trifluoro-acetyl)-piperazin-1-yl]-benzenesulfonyl chloride To a solution of 2 g of 2,2,2-trifluoro-1-(4-o-tolyl-piperazin-1-yl)-ethanone (7.35 mmol) in 5 mL of dichloromethane at −5° C. were slowly added 19.7 g of chlorosulfonic acid (169 mmol). After stirring for 2 h at −5° C., the reaction mixture continued stirring for 16 h, thereby slowly allowed to warm to room temperature. After cooling to 0° C., the reaction mixture was slowly added to a water/ice mixture. The aqueous phase was extracted five times with dichloromethane, the combined organic phases washed with aqueous sodium bicarbonate solution and saturated sodium chloride solution. The organic layer was dried over magnesium sulphate, filtered, and the solvent evaporated to yield 2.2 g of product as a white solid.

1.3 4-Methyl-N-(3-methoxymethyl-phenyl)-3-[4-(2,2,2-trifluoro-acetyl)-piperazin-1-yl-benzenesulfonamide 4-Methyl-3-(4-(2,2,2-trifluoroacetyl)piperazin-1-yl)benzene-1-sulfonyl chloride (0.150 mg, 0.405 mmol) were added to a solution of commercially available 3-(methoxymethyl) aniline (0.056 g, 0.405 mmol) in 2 mL pyridine. The reaction was stirred at room temperature for 18 h and the solvent evaporated under reduced pressure to yield 0.191 g of product which was used in the subsequent step without further purification.

ESI-MS: 471.2 [M+H]$^+$

1.4 N-(3-Methoxymethyl-phenyl)-4-methyl-3-piperazin-1-yl-benzenesulfonamide hydrochloride Aqueous ammonia (0.087 mL, 0.608 mmol) were added to a solution of N-(3-(methoxymethyl)phenyl)-4-methyl-3-(4-(2,2,2-trifluoroacetyl)piperazin-1-yl)benzenesulfonamide (0.191 g, 0.405 mmol) in 2 mL methanol and the reaction stirred for 18 h at room temperature. The solvent was evaporated and the residue purified via reversed-phase preparative HPLC. Fractions containing the product were combined, the pH adjusted to pH 7 with 5% aqueous sodium hydrogencarbonate solution, and extracted three times with dichloromethane. The combined organic layers were evaporated to dryness and the residue converted to the hydrochloride salt be addition of 2 N HCl in diethyl ether to yield 0.084 g of the desired product.

ESI-MS: 376.1 [M+H]$^+$ $^1$H-NMR (DMSO-d$_6$, 400 Hz): δ[ppm] 10.29 (s, 1H), 9.6 (s, 2H), 7.3-7.4 (m, 3H), 7.18 (m, 1H), 7.09 (s, 1H), 7.03 (d, 1H), 6.95 (d, 1H), 4.3 (s, 2H), 3.2 (s, 3H), 3.2 (m, 4H), 3.04 (m, 4H), 2.26 (s, 3H).

Example 2

N-(3-Methoxymethyl-phenyl)-4-methoxy-3-piperazin-1-yl-benzenesulfonamide hydrochloride

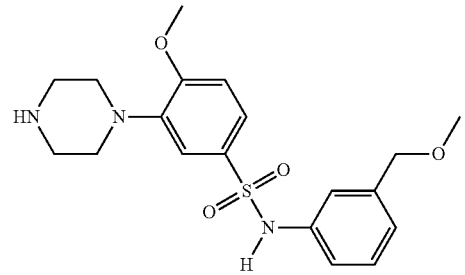 [SMILES: COCc1cccc(NS(=O)(=O)c2ccc(OC)c(N3CCNCC3)c2)c1]

4-Methoxy-3-[4-(2,2,2-trifluoro-acetyl)-piperazin-1-yl]-benzenesulfonyl chloride was prepared as described in Example 1, steps 1.1 and 1.2 by starting from commercially available 2-methoxy-phenyl-piperazine.

N-(3-Methoxymethyl-phenyl)-4-methoxy-3-piperazin-1-yl-benzenesulfonamide hydrochloride was obtained as described in Example 1, steps 1.3 and 1.4 by final reaction of N-(3-methoxymethyl-phenyl)-4-methoxy-3-[4-(2,2,2-trifluoro-acetyl)-piperazin-1-yl]-benzenesulfonamide with aqueous sodium hydroxide.

ESI-MS: 392.1 [M+H]$^+$ $^1$H-NMR (DMSO-d$_6$, 400 Hz): δ[ppm] 7.36 (d, 1H), 7.19 (s, 1H), 7.18 (d, 1H), 7.08 (s, 1H), 6.95-7.1 (m, 2H), 6.95 (d, 1H), 4.3 (s, 2H), 3.8 (s, 3H), 3.2 (s, 3H), 2.7-3.0 (m, 8H).

Example 3

4-Ethoxy-N-(3-methoxymethyl-phenyl)-3-piperazin-1-yl-benzenesulfonamide hydrochloride

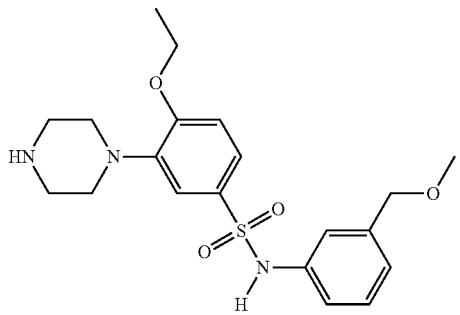 [SMILES: CCOc1ccc(S(=O)(=O)Nc2cccc(COC)c2)cc1N1CCNCC1]

4-Ethoxy-3-[4-(2,2,2-trifluoro-acetyl)-piperazin-1-yl-benzenesulfonyl chloride was prepared as described in example 1, steps 1.1 and 1.2 by starting from commercially available 2-ethoxy-phenyl-piperazine.

4-Ethoxy-N-(3-methoxymethyl-phenyl)-3-piperazin-1-yl-benzenesulfonamide hydrochloride was obtained as described in Example 1, steps 1.3 and 1.4 by final reaction of N-(3-methoxymethyl-phenyl)-4-ethoxy-3-[4-(2,2,2-trifluoro-acetyl)-piperazin-1-yl]-benzenesulfonamide with aqueous sodium hydroxide.

ESI-MS: 406.1 [M+H]$^+$ $^1$H-NMR (DMSO-d$_6$, 400 Hz): δ[ppm] 10.06 (broad, 1H), 8.8 (broad, 2H), 7.38 (d, 1H), 7.15-7.2 (m, 2H), 7.1 (m, 2H), 6.98 (m, 1H), 6.94 (m, 1H), 4.3 (s, 2H), 4.06 (m, 2H), 3.3 (m, 4H), 3.2 (s, 3H), 3.12 (m, 4H), 1.34 (m, 3H).

Example 4

4-Methoxy-N-(2-methoxymethyl-phenyl)-3-piperazin-1-yl-benzenesulfonamide hydrochloride

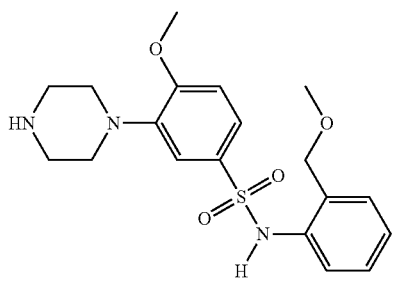 [SMILES: COCc1ccccc1NS(=O)(=O)c1ccc(OC)c(N2CCNCC2)c1]

The product was obtained as described in Example 1 by reaction of N-(2-methoxymethyl-phenyl)-4-methoxy-3-[4-(2,2,2-trifluoro-acetyl)-piperazin-1-yl]-benzenesulfonamide with aqueous sodium hydroxide.

ESI-MS: 392.1 [M+H]$^+$ $^1$H-NMR (DMSO-d$_6$, 400 Hz): δ[ppm] 9.55 (broad, 2H), 9.44 (broad, 1H), 7.34 (m, 1H), 7.33 (m, 1H), 7.15-7.25 (m, 3H), 7.1 (d, 1H), 6.9 (d, 1H), 4.32 (s, 2H), 3.86 (s, 3H), 3.1-3.25 (broad, 8H), 3.19 (s, 3H).

Example 5

N-(3-Ethoxymethyl-phenyl)-4-methoxy-3-piperazin-1-yl-benzenesulfonamide hydrochloride

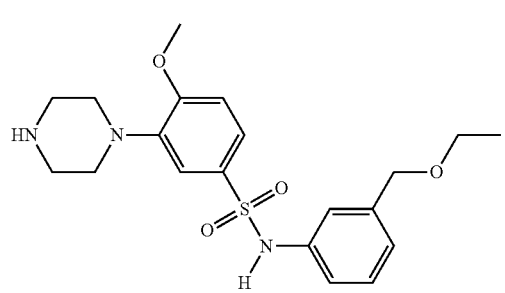 [SMILES: CCOCc1cccc(NS(=O)(=O)c2ccc(OC)c(N3CCNCC3)c2)c1]

The product was obtained as described in Example 1 by reaction of N-(3-ethoxymethyl-phenyl)-4-methoxy-3-[4-(2,2,2-trifluoro-acetyl)-piperazin-1-yl]-benzenesulfonamide with aqueous sodium hydroxide.

ESI-MS: 406.1 [M+H]$^+$ $^1$H-NMR (DMSO-d$_6$, 400 Hz): δ[ppm] 7.38 (m, 1H), 7.15-7.25 (m, 2H), 7.1 (s, 1H), 7.05-6.95 (m, 2H), 6.94 (d, 1H), 4.34 (s, 2H), 3.79 (s, 3H), 3.38 (m, 2H), 2.6-2.9 (broad, 8H), 1.1 (m, 3H).

Example 6

4-Methoxy-3-piperazin-1-yl-N-[3-(2,2,2-trifluoro-ethoxymethyl)-phenyl]-benzenesulfonamide hydrochloride

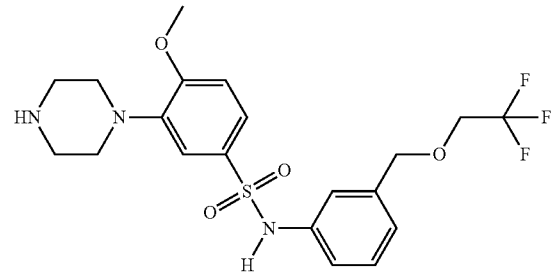 [SMILES: COc1ccc(S(=O)(=O)Nc2cccc(COCC(F)(F)F)c2)cc1N1CCNCC1]

The product was obtained as described in Example 1 by reaction of 4-methoxy-3-[4-(2,2,2-trifluoro-acetyl)-piperazin-1-yl]-N-[3-(2,2,2-trifluoro-ethoxymethyl)-phenyl]-benzenesulfonamide with aqueous sodium hydroxide.

ESI-MS: 460.1 [M+H]$^+$ $^1$H-NMR (DMSO-d$_6$, 400 Hz): δ[ppm] 7.38 (d, 1H), 7.15-7.25 (m, 2H), 7.13 (s, 1H), 7.08 (d, 1H), 7.05-6.95 (m, 2H), 4.57 (s, 2H), 4.0 (m, 2H), 3.8 (s, 3H), 2.9 (broad, 8H).

Example 7

4-Methoxy-N-(3-methoxymethyl-phenyl)-3-(4-methyl-piperazin-1-yl)-benzenesulfonamide hydrochloride

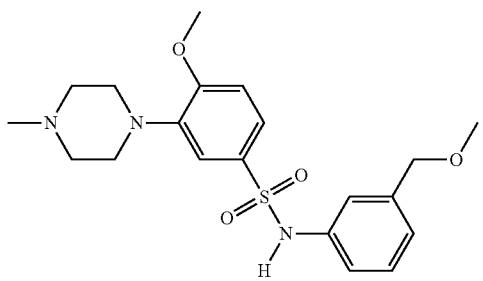

The product was obtained from N-methylation of Example 2 with aqueous formaldehyde and sodium tris-acetoxy-borohydride.

ESI-MS: 406.1 [M+H]$^+$ $^1$H-NMR (DMSO-d$_6$, 400 Hz): δ[ppm] 10.16 (s, 1H), 7.4 (d, 1H), 7.3 (s, 1H), 7.19 (m, 1H), 7.0-7.15 (m, 3H), 6.95 (d, 1H), 4.3 (s, 2H), 3.8 (s, 3H), 3.09-3.7 (very broad, 8H), 3.2 (s, 3H), 2.84 (s, 3H).

Example 8

4-Methoxy-N-[3-(1-methoxy-ethyl)-phenyl]-3-piperazin-1-yl-benzenesulfonamide hydrochloride

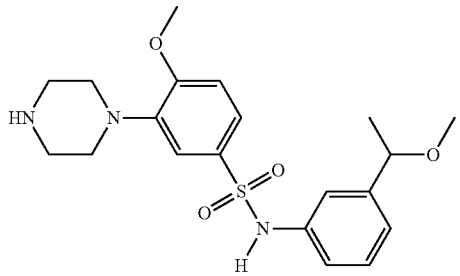 [SMILES: COc1ccc(S(=O)(=O)Nc2cccc(C(C)OC)c2)cc1N1CCNCC1]

The product was obtained as described in Example 1 by reaction of 4-methoxy-N-[3-(1-methoxy-ethyl)-phenyl]-3-[4-(2,2,2-trifluoro-acetyl)piperazin-1-yl]-benzenesulfonamide with aqueous sodium hydroxide.

ESI-MS: 406.2 [M+H]$^+$ $^1$H-NMR (DMSO-d$_6$, 400 Hz): δ[ppm] 7.36 (d, 1H), 7.25 (s, 1H), 7.18 (m, 1H), 7.0-7.1 (m, 3H), 6.93 (d, 1H), 4.17 (m, 1H), 3.79 (s, 3H), 3.05-3.2 (broad, 8H), 3.0 (s, 3H), 1.2 (d, 3H).

Example 9

3-[1,4]Diazepan-1-yl-4-methoxy-N-(3-methoxymethyl-phenyl)-benzenesulfonamide hydrochloride

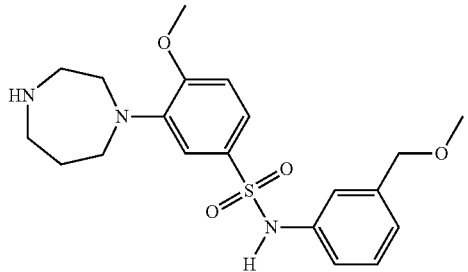 [SMILES: COCc1cccc(NS(=O)(=O)c2ccc(OC)c(N3CCCNCC3)c2)c1]

4-Methoxy-3-[4-(2,2,2-trifluoro-acetyl)-[1,4]diazepan-1-yl]-benzenesulfonyl chloride was prepared as described in example 1, steps 1.1 and 1.2 by starting from commercially available 1-(2-methoxy-phenyl)-[1,4]diazepane.

3-[1,4]Diazepan-1-yl-4-methoxy-N-(3-methoxymethyl-phenyl)-benzenesulfonamide hydrochloride was obtained as described in Example 1, steps 1.3 and 1.4 by reaction of 3-[4-(2,2,2-trifluoro-acetyl)-[1,4]diazepan-1-yl]-4-methoxy-N-(3-methoxymethyl-phenyl)-benzenesulfonamide with aqueous sodium hydroxide.

ESI-MS: 406.1 [M+H]$^+$ $^1$H-NMR (DMSO-d$_6$, 400 Hz): δ[ppm] 10.1 (s, 1H), 8.8 (s, 2H), 7.3 (d, 1H), 7.18 (s, 1H), 7.18 (m, 1H), 7.08 (s, 1H), 7.03 (m, 1H), 7.0 (m, 1H), 6.93 (m, 1H), 4.3 (s, 2H), 3.8 (s, 3H), 3.35 (m, 4H), 3.28 (m, 2H), 3.2 (s, 3H), 3.12 (m, 2H), 2.1 (m, 2H).

Example 10

4-Methoxy-N-(3-methoxymethyl-phenyl)-N-methyl-3-piperazin-1-yl-benzenesulfonamide hydrochloride

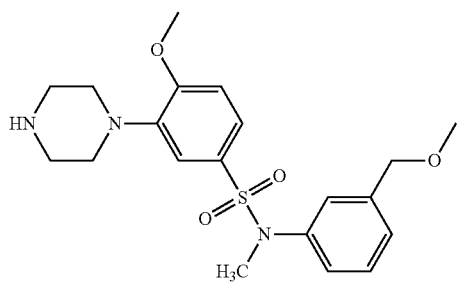 [SMILES: COCc1cccc(N(C)S(=O)(=O)c2ccc(OC)c(N3CCNCC3)c2)c1]

The product was obtained by reaction of 4-methoxy-N-(3-methoxymethyl-phenyl)-N-methyl-3-[4-(2,2,2-trifluoro-acetyl)piperazin-1-yl]-benzenesulfonamide with aqueous sodium hydroxide, reprotection of the piperazine nitrogen with the tert-butyloxycarbonyl protecting group, reaction of this intermediate with sodium hydride and methyl-iodide to methylate the sulfonamide nitrogen, followed by subsequent acidic deprotection of the tert-butyl-oxycarbonyl protecting group.

ESI-MS: 406.2 [M+H]$^+$ $^1$H-NMR (DMSO-d$_6$, 400 Hz): δ[ppm] 7.3 (m, 1H), 7.2 (m, 2H), 7.1 (d, 1H), 7.06 (s, 1H), 7.02 (d, 1H), 6.7 (s. 1H), 4.35 (s, 2H), 3.87 (s, 3H), 3.4 (broad, 4H), 3.25 (s, 3H), 3.05 (s, 3H), 2.75 (broad, 4H).

Example 11

N-(4-Methoxymethyl-phenyl)-4-methoxy-3-piperazin-1-yl-benzenesulfonamide trifluoroacetate

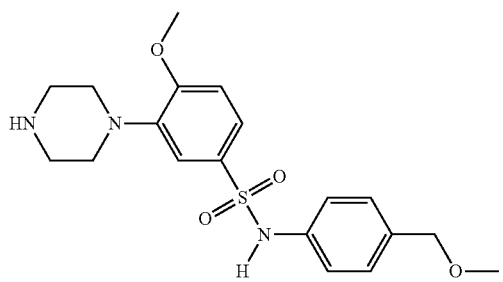 [SMILES: COCc1ccc(NS(=O)(=O)c2ccc(OC)c(N3CCNCC3)c2)cc1]

The product was obtained as described in Example 1 by reaction of N-(4-methoxymethyl-phenyl)-4-methoxy-3-[4-(2,2,2-trifluoro-acetyl)piperazin-1-yl]-benzenesulfonamide with aqueous sodium hydroxide.

ESI-MS: 392.1 [M+H]$^+$

The following compounds were prepared in analogy to the above examples.

Example 12

N-(2-Methoxymethyl-phenyl)-4-methyl-3-piperazin-1-yl-benzenesulfonamide hydrochloride

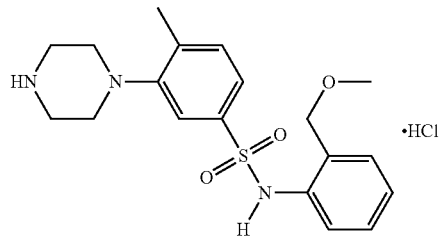 [SMILES: COCc1ccccc1NS(=O)(=O)c1ccc(C)c(N2CCNCC2)c1 ; Cl]

0.116 g of the product was obtained as described in Example 1 by reaction of N-(2-methoxymethyl-phenyl)-4-methyl-3-[4-(2,2,2-trifluoro-acetyl)piperazin-1-yl]-benzenesulfonamide with aqueous sodium hydroxide.

ESI-MS: 376.1 [M+H]$^+$

Example 13

N-(2-Methoxymethyl-phenyl)-4-ethoxy-3-piperazin-1-yl-benzenesulfonamide

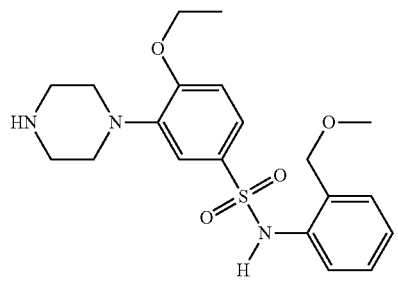 [SMILES: CCOc1ccc(S(=O)(=O)Nc2ccccc2COC)cc1N1CCNCC1]

0.074 g of the product was obtained as described in Example 1 by reaction of N-(2-methoxymethyl-phenyl)-4-ethoxy-3-[4-(2,2,2-trifluoro-acetyl)piperazin-1-yl]-benzenesulfonamide with aqueous sodium hydroxide.

ESI-MS: 406.1 [M+H]$^+$

Example 14

N-(2-Methoxymethyl-phenyl)-4-ethoxy-3-(4-methyl-piperazin-1-yl)-benzenesulfonamide hydrochloride

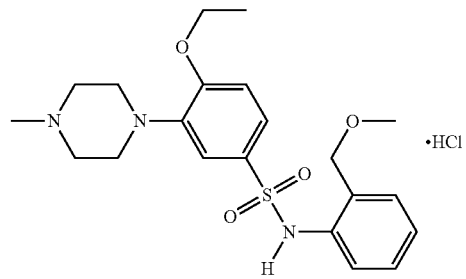 [SMILES: CCOc1ccc(S(=O)(=O)Nc2ccccc2COC)cc1N1CCN(C)CC1 ; Cl]

0.105 g of the product was obtained as described in Example 1 by reaction of N-(2-methoxymethyl-phenyl)-4-ethoxy-3-[4-(2,2,2-trifluoro-acetyl)piperazin-1-yl]-benzenesulfonamide with aqueous sodium hydroxide and subsequent N-methylation via reductive amination.

ESI-MS: 420.2 [M+H]$^+$

Example 15

N-(3-Methoxymethyl-phenyl)-4-ethoxy-3-(4-methyl-piperazin-1-yl)-benzenesulfonamide hydrochloride

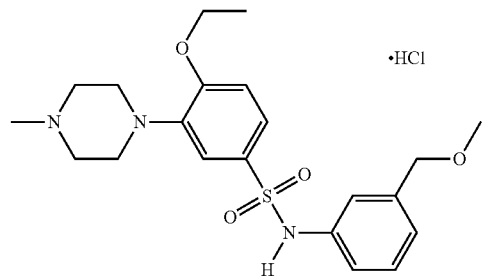

0.180 g of the product was obtained as described in Example 1 by reaction of N-(3-methoxymethyl-phenyl)-4-ethoxy-3-[4-(2,2,2-trifluoro-acetyl)piperazin-1-yl]-benzenesulfonamide with aqueous sodium hydroxide and subsequent N-methylation via reductive amination.

ESI-MS: 420.2 [M+H]$^+$

Example 16

N-(3-Methoxymethyl-phenyl)-4-methyl-3-(4-methyl-piperazin-1-yl)-benzenesulfonamide hydrochloride

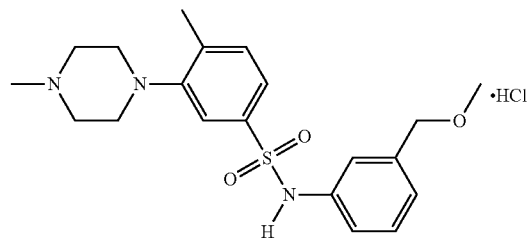

0.012 g of the product was obtained as described in Example 1 by reaction of N-(3-methoxymethyl-phenyl)-4-methyl-3-[4-(2,2,2-trifluoro-acetyl)piperazin-1-yl]-benzenesulfonamide with aqueous sodium hydroxide and subsequent N-methylation via reductive amination.

ESI-MS: 390.1 [M+H]$^+$

Example 17

N-(2-Methoxymethyl-phenyl)-4-methoxy-3-(4-methyl-piperazin-1-yl)benzenesulfonamide hydrochloride

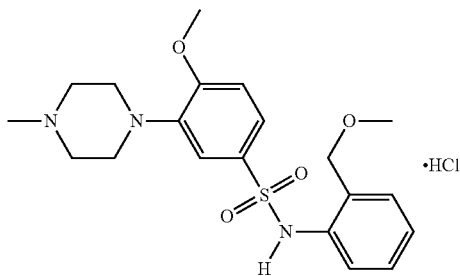 [SMILES: COCc1ccccc1NS(=O)(=O)c1ccc(OC)c(N2CCN(C)CC2)c1 ; Cl]

0.056 g of the product was obtained as described in Example 1 by reaction of N-(2-methoxymethyl-phenyl)-4-methoxy-3-[4-(2,2,2-trifluoro-acetyl)piperazin-1-yl]-benzenesulfonamide with aqueous sodium hydroxide and subsequent N-methylation via reductive amination.

ESI-MS: 406.1 [M+H]$^+$

Example 18

N-(2-Methoxymethyl-phenyl)-4-methyl-3-(4-methyl-piperazin-1-yl)-benzenesulfonamide hydrochloride

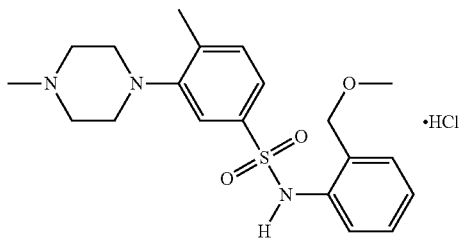 [SMILES: COCc1ccccc1NS(=O)(=O)c1ccc(C)c(N2CCN(C)CC2)c1 ; Cl]

0.022 g of the product was obtained as described in Example 1 by reaction of N-(2-methoxymethyl-phenyl)-4-methyl-3-[4-(2,2,2-trifluoro-acetyl)piperazin-1-yl]-benzenesulfonamide with aqueous sodium hydroxide and subsequent N-methylation via reductive amination.

ESI-MS: 390.2 [M+H]$^+$

II. BIOLOGICAL INVESTIGATIONS

Displacement of radioligands binding to the following cloned human receptors

1. Preparation of Membranes by Ultrasonic Treatment and Differential Centrifugation Cells from stable clonal cell lines expressing the corresponding receptor (5-HT$_6$, α$_1$-adrenergic, dopamine D$_2$ or histamine H$_1$ receptors) were washed with PBS (w/o Ca$^{++}$, Mg$^{++}$) and harvested in PBS with 0.02% EDTA. The cells were collected by centrifugation at 500 g for 10 min. at 4° C., washed with PBS and centrifuged (500 g, 10 min. 4° C.). The pellets were stored at −80° C. until use. For membrane preparation, the thawed cell pellet was resuspended in ice-cold sucrose buffer (0.25 M sucrose, 10 mM Hepes (pH 7.4), 1 mM phenylmethylsulfonyl fluoride (PMSF) in DMSO, 5 μg/ml Pepstatin-A, 3 mM EDTA, 0.025% Bacitracin) and homogenized with a Branson Sonifier W-250 (Settings: Timer 4; Output Control 3; Duty Cycle constant; 2 to 3 cycles). Cell disruption was checked with the aid of a microscope. Remaining unbroken cells were pelleted at 1.000 g for 10 min. at 4° C. The sucrose buffer supernatant was then centrifuged at 60.000 g for 1 h at 4° C. (Beckman Ultrazentrifuge XL 80). The pellet was resuspended in 30 ml ice-cold Tris buffer (20 mM TRIS (pH 7.4), 5 μg/ml Pepstatin A, 0.1 mM PMSF, 3 mM EDTA) by pipetting through a 10 ml serological pipet and centrifuged for 1 h at 4° C. at 60.000 g. A final resuspension was performed in a small volume of ice-cold Tris buffer (see above) by pressing through a serological pipet followed by ultrasonic treatment with a Branson Sonifier W-250 (Settings: Timer 1; Output Control 3; Duty Cycle constant; 1 cycle). Protein concentration was determined (BCA-Kit; Pierce) and aliquots stored at −80° C. or in liquid nitrogen for long-term storage.

2. Receptor Binding Experiments

All receptor binding experiments were carried out in the corresponding assay buffer in a total volume of 200 μl in the presence of various concentrations of test compound (10$^{-5}$ M to 10$^{-9}$ M, tenfold serial dilution, duplicate determinations). The assays were terminated by filtration on polyethylenimine (PEI 0.1% or 0.3%) presoaked Packard Unifilter Plates (GF/C or GF/B) with a Tomtec Machin U 96well-plate harvester. After the plates had been dried for 2 h at 55° C. in a drying chamber scintillation cocktail (BetaPlate Scint; PerkinElmer) was added. Radioactivity was measured in a Microbeta Trilux two hours after the addition of the scintillation mixture. Data derived from liquid scintillation counting were analysed by iterative non-linear regression analysis with the use of the Statistical Analysis System (SAS): a program similar to "LIGAND" as described by Munson and Rodbard (Analytical Biochemistry 107, 220-239 (1980).

a) 5-HT$_6$ Receptor Binding Assay

HEK293 cells stably expressing the h-5-HT$_6$ receptor (NCBI Reference Sequence XM 001435) were cultured in RPMI1640 medium supplemented with 25 mM HEPES, 10% fetal calf serum and 1-2 mM glutamine. The membrane preparation was performed as described in section 1. For these membranes a K$_D$ of 1.95 nM for [$^3$H]-LSD (Lysergic Acid Diethylamide; Amersham, TRK1038) was determined by means of saturation binding experiments. On the day of the assay, the membranes were thawed, diluted in assay buffer (50 mM Tris-HCl, 5 mM CaCl$_2$, 0.1% ascorbic acid, 10 μM pargyline, pH 7.4) to a concentration of 8 μg protein/assay and homogenized by gentle vortexing For inhibition studies, 1 nM [$^3$H]-Lysergic Acid Diethylamide was incubated in the presence of various concentrations of test compound in assay buffer. Non-specific binding was defined with 1 μM methiothepin. The binding reaction was carried out for 3.5 h at room temperature. During the incubation, the plates were shaken on a plate shaker at 100 rpm and terminated by filtration on Packard Unifilter GF/C (0.1% PEI) plates, followed by 2 wash cycles with ice-cold 50 mM Tris-HCl, 5 mM CaCl$_2$.

b) Dopamine D$_2$ Receptor Binding Assay

HEK293 cells stably expressing the dopamine D$_2$ receptor (NCBI Reference Sequence NM_000795) were cultured in RPMI1640 medium supplemented with 25 mM HEPES, 10% fetal calf serum and 1-2 mM glutamine. The membrane preparation was performed as described in section 1. For these membranes a $K_D$ of 0.22 nM for [$^{125}$I]-iodospiperone (PerkinElmer Life Sciences, NEX284) was determined by means of saturation binding experiments. On the day of the assay, the membranes were thawed, diluted in assay buffer (50 mM Tris-HCl, 120 mM NaCl, 5 mM MgCl$_2$, 5 mM KCl, 1.5 mM CaCl$_2$, pH 7.4) to a concentration of 15 µg protein/assay and homogenized by gentle vortexing. For inhibition studies, 0.01 nM [$^{125}$I]-iodospiperone (PerkinElmer Life Sciences, NEX284) was incubated in the presence of various concentrations of test compound in assay buffer. Non-specific binding was defined with 1 µM haloperidol. The binding reaction was carried out for 1 h at room temperature and terminated by filtration on Packard Unifilter GF/B (0.1% PEI) plates, followed by 6 wash cycles with an ice-cold 7% polyethylenglycol solution.

c) $\alpha_1$-Adrenergic Receptor Binding Assay

CHO-K$_1$ cells stably expressing the $\alpha_1$-adrenergic receptor (NCBI Reference Sequence NM_033303) were cultured in RPMI1640 medium supplemented with 25 mM HEPES, 10% fetal calf serum and 1-2 mM glutamine. The membrane preparation was performed as described in section 1. For these membranes a $K_D$ of 0.12 nM for [$^3$H]-prazosine (PerkinElmer Life Sciences, NET823) was determined by means of saturation binding experiments. On the day of the assay, the membranes were thawed, diluted in assay buffer (50 mM Tris-HCl, pH 7.4) to a concentration of 4 µg protein/assay and homogenized by gentle vortexing. For inhibition studies, 0.1 nM [$^3$H]-prazosine (PerkinElmer Life Sciences, NET823) was incubated in the presence of various concentrations of test compound in assay buffer. Non-specific binding was defined with 1 µM phentolamine. The binding reaction was carried out for 1 h at room temperature and terminated by filtration on Packard Unifilter GF/C (0.1% PEI) plates, followed by 3 wash cycles with ice-cold assay buffer.

d) H$_1$ Receptor Binding Assay

CHO-K$_1$ cells stably expressing the histamine H$_1$ receptor (Euroscreen-ES-390-C, NCBI Reference Sequence NM_000861) were cultured in RPMI1640 medium supplemented with 25 mM HEPES, 10% fetal calf serum and 1-2 mM glutamine. The membrane preparation was performed as described in section 1. For these membranes a $K_D$ of 0.83 nM for [$^3$H]-pyrilamine (PerkinElmer Life Sciences, NET594) was determined by means of saturation binding experiments. On the day of the assay, the membranes were thawed, diluted in assay buffer (50 mM Na$_2$HPO$_4$, 50 mM KH$_2$PO$_4$, pH 7.4) to a concentration of 6 µg protein/assay and homogenized by gentle vortexing. For inhibition studies, 1 nM [$^3$H]-pyrilamine (PerkinElmer Life Sciences, NET594) was incubated in the presence of various concentrations of test compound in assay buffer. Non-specific binding was defined with 1 µM pyrilamine. The binding reaction was carried out for 50 minutes at room temperature and terminated by filtration on Packard Unifilter GF/C (0.3% PEI) plates, followed by 2 wash cycles with ice-cold assay buffer.

3. Data Analysis

Data derived from liquid scintillation counting were analyzed by iterative non-linear regression analysis with the use of the Statistical Analysis System (SAS): a program similar to "LIGAND" as described by Munson and Rodbard (Anal. Biochem. 1980, 107, 220-239). Fitting was performed according to formulae described by Feldman (Anal. Biochem. 1972, 48, 317-338). IC$_{50}$, nH and K$_i$ values were expressed as geometrical mean. For receptors with a low affinity for the test compound, where the highest tested compound concentration inhibited less than 30% of specific radioligand binding, K$_i$-values were determined according to the equation of Cheng and Prusoff (Biochem. Pharmacol. 1973, 22, 2099-2108) and expressed as greater than (>).

The results of the receptor binding studies are expressed as receptor binding constants K$_i$(5-HT$_6$), K$_i$(D$_2$), K$_i$($\alpha_1$-adrenergic) and K$_i$(H$_1$), respectively, as described herein before, and given in table I.

In these tests, the compounds according to the invention exhibit very good affinities for the 5-HT$_6$ receptor (K$_i$<250 nM or <50 nM or <20 nM and frequently <10 nM). Furthermore those compounds bind selectively to the 5-HT$_6$ receptor, as compared to the affinity for the D$_2$, the $\alpha_1$-adrenergic or the H$_1$ receptors. These compounds exhibit little affinities for the D$_2$, $\alpha_1$-adrenergic or H$_1$ receptors (K$_i$>250 nM or >1000 nM and frequently >10000 nM).

Example 1: Ki (5HT$_6$) <10 nM
Example 2: Ki (5HT$_6$) <10 nM
Example 3: Ki (5HT$_6$) <10 nM
Example 4: Ki (5HT$_6$) <10 nM
Example 5: Ki (5HT$_6$) <10 nM
Example 6: Ki (5HT$_6$) <10 nM
Example 7: Ki (5HT$_6$) <10 nM
Example 8: Ki (5HT$_6$) <20 nM
Example 9: Ki (5HT$_6$) <20 nM
Example 10: Ki (5HT$_6$) <100 nM
Example 11: Ki (5HT$_6$) <100 nM
Example 12: Ki (5-HT$_6$) <100 nM
Example 13: Ki (5-HT$_6$) <10 nM
Example 14: Ki (5-HT$_6$) <10 nM
Example 15: Ki (5-HT$_6$) <10 nM
Example 16: Ki (5-HT$_6$) <100 nM
Example 17: Ki (5-HT$_6$) <10 nM
Example 18: Ki (5-HT$_6$) <100 nM 3. Determination of the Metabolic Stability The metabolic stability of the compounds of the invention was determined in the following assay by analyzing the microsomal half-life. The test substances are incubated in a concentration of 0.5 µM as follows:

0.5 µM test substance is preincubated together with liver microsomes of various species (0.25 mg of protein/ml) in 0.05M potassium phosphate buffer pH 7.4 in microtiter plates at 37° C. for 5 min. The reaction is started by adding NADPH (1 mg/mL). Aliquots are taken after 0, 5, 10, 15, 20 and 30 min, and the reaction is stopped with the same volume of acetonitrile and cooled down. The remaining test compound concentrations are being determined by liquid chromatography—mass spectrometry analysis. Intrinsic clearance values are calculated using the elimination rate constant of test compound depletion.

We claim:

1. N-Phenyl-(homo)piperazinyl-benzenesulfonyl or benzenesulfonamide compounds of formula I the stereoisomers, N-oxides, tautomers and/or physiologically tolerated acid addition salts thereof; and the compounds of the formula I, wherein at least one of the atoms has been replaced by its stable, non-radioactive isotope,
wherein X is a bond or $NR^4$;
$R^1$ is selected from the group consisting of $C_1$-$C_4$-alkyl and fluorinated $C_1$-$C_4$-alkyl;
$R^2$ is selected from the group consisting of hydrogen and $C_1$-$C_4$-alkyl;
$R^3$ is selected from the group consisting of hydrogen, halogen, $C_1$-$C_4$-alkyl, fluorinated $C_1$-$C_4$-alkyl, $C_1$-$C_4$-alkoxy and fluorinated $C_1$-$C_4$-alkoxy;
$R^4$ is selected from the group consisting of hydrogen, $C_1$-$C_4$-alkyl and fluorinated $C_1$-$C_4$-alkyl;
$R^5$ is a group -A-[O—B]$_p$—O—$R^7$, wherein
A and B are independently of each other $C_1$-$C_4$-alkylene or fluorinated $C_1$-$C_4$-alkylene;
$R^7$ is $C_1$-$C_4$-alkyl or fluorinated $C_1$-$C_4$-alkyl; and
p is 0, 1, 2, 3, 4, 5 or 6;
$R^6$ is selected from the group consisting of halogen, $C_1$-$C_2$-alkyl, fluorinated $C_1$-$C_2$-alkyl, $C_1$-$C_2$-alkoxy and fluorinated $C_1$-$C_2$-alkoxy;
m is 0, 1 or 2; and
n is 1 or 2.

2. The compounds of claim 1, where A is $C_1$-$C_2$-alkylene.

3. The compounds of claim 2, where A is methylene ($CH_2$) or 1,1-ethylene [$CH(CH_3)$].

4. The compounds of claim 1, where B is $C_2$-$C_3$-alkylene.

5. The compounds of claim 1, where p is 0.

6. The compounds of claim 1, where $R^7$ is $C_1$-$C_2$-alkyl or fluorinated $C_1$-$C_2$-alkyl.

7. The compounds claim 1, where $R^5$ is selected from the group consisting of $C_1$-$C_2$-alkoxy-methyl, 1-($C_1$-$C_2$-alkoxy)-ethyl, (fluorinated $C_1$-$C_2$-alkoxy)-methyl and 1-(fluorinated $C_1$-$C_2$-alkoxy)-ethyl and is preferably methoxymethyl, ethoxymethyl, 2,2,2-trifluoroethoxymethyl or 1-methoxyethyl.

8. The compounds of claim 1, where $R^5$ is bound in the 2- or 3-position, relative to the 1-position of the sulfonylamino group SO—$NR^4$.

9. The compounds of claim 1, where $R^1$ is $C_1$-$C_4$-alkyl.

10. The compounds of claim 1, where $R^2$ is hydrogen.

11. The compounds of claim 1, where $R^3$ is selected from the group consisting of methoxy, ethoxy, methyl and ethyl and is preferably methoxy, ethoxy or methyl.

12. The compounds of claim 1, where X is $NR^4$.

13. The compounds of claim 1, where $R^4$ is hydrogen or $C_1$-$C_4$-alkyl, preferably hydrogen or methyl.

14. The compounds of claim 1, where $R^6$ is selected from the group consisting of F, Cl, methyl, difluoromethyl, trifluoromethyl, methoxy, difluoromethoxy and trifluoromethoxy.

15. The compounds of claim 1, where m is 0.

16. The compounds of claim 1, where n is 1.

17. The compounds of claim 1, wherein at least one hydrogen atom has been replaced by a deuterium atom.

18. A pharmaceutical composition comprising at least one compound of claim 1, a stereoisomer, N-oxide, tautomer and/or physiologically tolerated acid addition salt thereof, and at least one physiologically acceptable carrier and/or auxiliary substance.

19. The compounds of claim 1, where $R^1$ is methyl.

20. The compounds of claim 1 or the stereoisomers, N-oxides, tautomers or physiologically tolerated acid addition salts thereof, selected from the group consisting of:
  4-Methoxy-N-(3-methoxymethyl-phenyl)-3-(4-methylpiperazin-1-yl)-benzenesulfonamide hydrochloride;
  N-(2-Methoxymethyl-phenyl)-4-ethoxy-3-(4-methyl-piperazin-1-yl)-benzenesulfonamide hydrochloride;
  N-(3-Methoxymethyl-phenyl)-4-ethoxy-3-(4-methyl-piperazin-1-yl)-benzenesulfonamide hydrochloride;
  N-(3-Methoxymethyl-phenyl)-4-methyl-3-(4-methyl-piperazin-1-yl)-benzenesulfonamide hydrochloride;
  N-(2-Methoxymethyl-phenyl)-4-methoxy-3-(4-methylpiperazin-1-yl)benzenesulfonamide hydrochloride; and
  N-(2-Methoxymethyl-phenyl)-4-methyl-3-(4-methyl-piperazin-1-yl)-benzenesulfonamide hydrochloride.

* * * * *